(12) United States Patent
Fischer et al.

(10) Patent No.: US 9,221,868 B2
(45) Date of Patent: Dec. 29, 2015

(54) URIDINE DI- OR TRI-PHOSPHATE DERIVATIVES AND USES THEREOF

(75) Inventors: Bilha Fischer, Shoham (IL); Jesus Jeronimo Pintor, Madrid (ES); Shay Elyahu, Ramat-Efal (IL); Tamar Ginsburg-Shmuel, Ra'anana (IL)

(73) Assignees: BAR-ILAN UNIVERSITY (IL); UNIVERSIDAD COMPLUTENSE DE MADRID (ES)

( * ) Notice: Subject to any disclaimer, the term of this patent is extended or adjusted under 35 U.S.C. 154(b) by 215 days.

(21) Appl. No.: 13/990,491

(22) PCT Filed: Dec. 1, 2011

(86) PCT No.: PCT/IL2011/000913
§ 371 (c)(1),
(2), (4) Date: Aug. 2, 2013

(87) PCT Pub. No.: WO2012/073237
PCT Pub. Date: Jun. 7, 2012

(65) Prior Publication Data
US 2013/0324495 A1 Dec. 5, 2013

Related U.S. Application Data

(60) Provisional application No. 61/344,972, filed on Dec. 1, 2010, provisional application No. 61/467,108, filed on Mar. 24, 2011.

(51) Int. Cl.
| | | |
|---|---|---|
| C07H 19/04 | (2006.01) |
| A01N 43/04 | (2006.01) |
| A61K 31/70 | (2006.01) |
| C07H 23/00 | (2006.01) |
| C07F 9/6558 | (2006.01) |
| C07H 19/10 | (2006.01) |
| C07H 21/02 | (2006.01) |

(52) U.S. Cl.
CPC ............ C07H 23/00 (2013.01); C07F 9/65586 (2013.01); C07H 19/10 (2013.01); C07H 21/02 (2013.01)

(58) Field of Classification Search
CPC .... C07F 9/65586; C07H 23/00; C07H 21/02; C07H 19/10
See application file for complete search history.

(56) References Cited

U.S. PATENT DOCUMENTS 7,084,128 B2   8/2006  Yerxa et al.
7,368,439 B2 *  5/2008  Fischer et al. .................. 514/47

FOREIGN PATENT DOCUMENTS

WO    2009066298 A1    5/2009

OTHER PUBLICATIONS

Ginsburg-Shmuel T., Haas M., Schumann M., Reiser G., Kalid O., Stern N., Fischer B., "5-OMe-UDP is a potent and selective P2Y6-receptor agonist". Journal of Medicinal Chemistry, 53, pp. 1673-1685. (2010).
International Search Report for corresponding application No. PCT/IL2011/000913 filed Dec. 1, 2011; Mail date Mar. 5, 2012.
Written Opinion for corresponding application No. PCT/IL2011/000913 filed Dec. 1, 2011; Mail date Mar. 5, 2012.
Barral K. et al; "Synthesis, in vitro antiviral evaluation, and stability studies of novel alpha-borano-nucleotide analogues of 9-[2-(Phosphonomethoxy)ethyl]adenine and (R)-9-[2-(phosphonomethoxy)propyl]adenine". Journal of medicinal chemistry, 49, pp. 7799-7806. (2006).
Besada P. et al; "Structure-activity relationships of uridine 5'-diphosphate analogues at the human P2Y6 receptor". Journal of medicinal chemistry, 49, pp. 5532-5543. (2006).
Boyle N.A et al; "Synthesis of 2',3'-dideoxynucleoside 5'-alpha-P-borano-beta,gamma-(difluoromethylene) triphosphates and their inhibition of HIV-1 reverse transcriptase". Journal of medicinal chemistry, 48, pp. 2695-2700. (2006).
Costanzi S. et al; "Human P2Y6 receptor: molecular modeling leads to the rational design of a novel agonist based on a unique conformational preference". Journal of medicinal chemistry, 48, pp. 8108-8111. (2005).
Crooke A.et al; "Nucleotides in ocular secretions: Their role in ocular physiology". Pharmacology & Therapeutics 119, pp. 55-73. (2005).
Chesterfield J.H.et al; "Pyrimidines. XI. Synthesis of 5-hydroxypyrimidine and related compounds". Journal of medicinal chemistry, pp. 4590-4594. (1960).
El-Tayeb A. et al; "Synthesis and structure-activity relationships of uracil nucleotide derivatives and analogues as agonists at human P2Y2, P2Y4, and P2Y6 receptors". Journal of medicinal chemistry, 49,pp. 7076-7087. (2006).
Eliahu S.E. et al; "Identification of hydrolytically stable and selective P2Y1 receptor agonists". European Journal of Medicinal Chemistry, 44, pp. 1525-1536. (2009).
Eliahu S.E. et al; "2-MeS-β,γ-CCl2-ATP is a potent agent for reducing intraocular pressure". Journal of medicinal chemistry, 53, pp. 3305-3319. (2010).
Ginsburg-Shmuel T. et al; "5-OMe-UDP is a potent and selective P2Y6-receptor agonist". Journal of medicinal chemistry,53, pp. 1673-1685. (2010).

(Continued)

*Primary Examiner* — Lawrence E Crane
(74) *Attorney, Agent, or Firm* — Cantor Colburn LLP

(57) ABSTRACT

The disclosure provides particular uridine di- and tri-phosphate compounds of Formula I, and pharmaceutical compositions thereof. The definitions of variables such as R, Y, B, m, $Z_1$, $Z_2$, and $Z_3$ are as provided in the disclosure. These compounds are useful for treatment of diseases, disorders and conditions modulated by $P2Y_6$ receptors, and particularly for lowering intraocular pressure and thereby treating ocular hypertension and/or glaucoma.

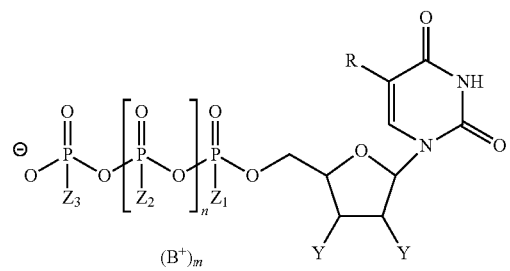

19 Claims, 5 Drawing Sheets

(56) References Cited

OTHER PUBLICATIONS

Griffin B.E. et al; "The synthesis of oligoribonucleotides. II. Methoxymethylidene derivatives of ribonucleosides and 5'-ribonucleotides". Tetrahedron, 23, pp. 2301-2313. (1967).

Guzman-Aranguez A. et al; "Dinucleoside polyphosphates in the eye: from physiology to therapeutics". Progress in Retinal and Eye Research. 26, pp. 674-687. (2007).

Jacobson K.A. et al; "Development of selective agonists and antagonists of P2Y receptors". Purinergic Signalling, 5, pp. 75-89.(2009).

Jacobson K.A., et al; "P2Y nucleotide receptors: promise of therapeutic applications". Drug Discovery Today,15,pp. 570-578.(2010).

Ko H. et al; "Synthesis and potency of novel uracil nucleotides and derivatives as P2Y2 and P2Y6 receptor agonists". Bioorganic & Medicinal Chemistry, 16, pp. 6319-6332. (2008).

Kowalska J. et al; "A simple and rapid synthesis of nucleotide analogues containing a phosphorothioate moiety at the terminal position of the phosphate chain". Tetrahedron Letters, 48, pp. 5475-5479. (2007).

Major D.T.et al; "Molecular Recognition in Purinergic Receptors. 2. Diastereoselectivity of the h-P2Y1-Receptor". Journal of medicinal chemistry, 47,pp. 4405-4416. (2004).

Maruoka H. et al; "Pyrimidine ribonucleotides with enhanced selectivity as P2Y6 receptor agonists: novel 4-alkyloxyimino, (S)-methanocarba, and 5'-triphosphate γ-ester modifications". Journal of medicinal chemistry, 53, pp. 4488-4501. (2010).

Misiura K. et al; "Synthesis of nucleoside •-thiotriphosphates/ia an oxathiaphospholane approach". Orgenic Letters, , 7, pp. 2217-2220. (2005).

Niedballa U. et al; "A general synthesis of N-glycosides. 6. On the mechanism of the stannic chloride catalyzed silyl Hilbert-Johnson reaction". Journal of. Orgenic Chemistry, 41, pp. 2084-2086.(1976).

Peral A. et al;,"Adenine nucleotide effect on intraocular pressure: Involvement of the parasympathetic nervous system". Experimental Eye Research, 89, pp. 63-70. (2009).

Pintor J. et al; "Adenosine tetraphosphate, Ap4, a physiological regulator of intraocular pressure in normotensive rabbit eyes". The Journal of PharMmacology and Experimental Therapeutics, 308, pp. 468-473.(2004).

Pintor J. "Adenine nucleotides and dinucleotides as new substances for the treatment of ocular hypertension and glaucoma". Current opinion in investigational drugs ,6, pp. 76-80.(2005).

Shaver S.R. et al; "Structure-activity relationships of dinucleotides: Potent and selective agonists of P2Y receptors. Purinergic Signal" Purinergic Signalling ,1, pp. 183-191 .(2005).

Stout M.G. et al; "Synthesis of some 5-methoxypyrimidine nucleosides". Journal of Heterocyclic Chemistry, 9, pp. 545-549. (1972).

Yerxa B.R. et al; "Pharmacology of INS37217 [P1-(uridine 5')-P4-(2'-deoxycytidine 5')tetraphosphate, tetrasodium salt], a next-generation P2Y2 receptor agonist for the treatment of cystic fibrosis". The Journal of PharMmacology and Experimental Therapeutics, 302, pp. 871-880. (2002).

International Preliminary Report on Patentability for corresponding application No. PCT/IL2011/000913 filed Dec. 1, 2011; Mail date Jun. 4, 2013.

\* cited by examiner

URIDINE DI- OR TRI-PHOSPHATE DERIVATIVES AND USES THEREOF

CROSS REFERENCES TO RELATED APPLICATIONS

The present application is a 371 national stage of International Application No. PCT/IL2011/000913, filed Dec. 1, 2011, and claims the benefit of U.S. Provisional Patent Application No. 61/344,972, filed Dec. 1, 2010, and U.S. Provisional Patent Application No. 61/467,108, filed Mar. 24, 2011, the entire content of each and all these applications being herewith incorporated by reference in their entirety as if fully disclosed herein.

TECHNICAL FIELD

The present invention relates to uridine di- and tri-phosphate derivatives and to pharmaceutical compositions thereof. The compounds are useful for treatment of diseases, disorders and conditions modulated by $P2Y_6$ receptors, and particularly for lowering intraocular pressure and thereby treating ocular hypertension and/or glaucoma.

BACKGROUND ART

Extracellular nucleotides that activate G protein-coupled P2Y receptors (P2YRs) are attractive pharmaceutical targets due to their ability to modulate various functions in many tissues and organs under normal and pathophysiological conditions (Hillmann et al., 2009; Burnstock and Verkhratsky, 2009). Extracellular nucleotides and dinucleotides have been shown to play a role in ocular physiology and physiopathology (Crooke et al., 2008), and have been suggested as therapeutic agents for dry eye, retinal detachment and glaucoma (Guzman-Aranguez et al., 2007).

Ocular hypertension, the most common cause of glaucoma, is a target for agents that reduce intraocular pressure (IOP) (Pintor, 2005). When topically applied to New Zealand white rabbits, some nucleotides, e.g., diadenosine triphosphate and diadenosine pentaphosphate, produce an increase in IOP while others such as ATP, adenosine tetraphosphate and diadenosine tetraphosphate decrease IOP (Peral et al., 2009; Pintor et al., 2003, 2004).

Receptors for extracellular nucleotides including $P2Y_1$, $P2Y_2$ and $P2Y_4$ have been identified in trabecular meshwork (TM) cells, an area of tissue in the eye that is responsible for draining the aqueous humor (Soto et al., 2005). Among these P2YR subtypes, activation of the $P2Y_1R$ by the selective agonist 2-MeS-ADP reduces aqueous humor outflow in bovine ocular. Other studies have reported the presence of $P2Y_1$ and $P2Y_2$ receptors in bovine TM cells, and of $P2Y_1$, $P2Y_4$ and $P2Y_{11}$ receptors in a human TM cell line (Crosson et al., 2004).

Lately, the structure-activity relationship of $P2Y_6$-R agonists and antagonists, and the molecular modeling of the $P2Y_6$-R involved in the reduction of IOP have been extensively investigated (El-Tayeb et al., 2006; Jacobson et al., 2009; Costanzi et al., 2005; Maruoka et al., 2010; Besada et al., 2006); however, no potent and selective $P2Y_6$-R agonist or antagonist has yet been identified. The development of agonists for the $P2Y_6$-R included modification of the UDP phosphate chain, ribose ring, and base. Different uracil modifications have been performed over the last years in an attempt to identify agonists which will be more potent than the endogenous ligand UDP (Maruoka et al., 2010; Ginsburg-Shmuel et al., 2010; Ko et al., 2008).

The therapeutic potential of nucleotides in general, and for the treatment of glaucoma in particular, is limited, since they are degraded by extracellular enzymes, which reduce their potency, efficacy and duration of action. In addition, although nucleotides are chemically stable in a pH range of 4-11 (El-Tayeb et al., 2006), they are rapidly degraded at a more acidic or basic pH. Nucleotides are hydrolyzed enzymatically by the ecto-nucleoside triphosphate diphosphohydrolase family of ectonucleotidases, i.e., e-NTPDase and alkaline phosphatases (Nahum et al., 2002), and ecto-nucleotide pyrophosphatases/phosphodiesterases, i.e., e-NPPs (Grobben et al., 2000; Zimmermann, 2001). Therefore, there is a need for identification of both enzymatically and chemically stable nucleotide scaffolds that can be used to develop selective and potent P2YR agonists.

A few attempts to improve the stability of nucleotides have been reported (Cusack et al., 1987; Misiura et al., 2005; Kowalska et al., 2007), including the use of phosphate bioisosteres of nucleotides such as phosphonate (Eliahu et al., 2009; Joseph et al., 2004), phosphoramide (Zhou et al., 2005), and boranophosphate analogues (Nahum et al., 2002; Boyle et al., 2005; Barral et al., 2006; Eliahu et al., 2009).

A second strategy for enhancing stability of potential P2Y-R agonists is the use of dinucleotides, e.g., diuridine triphosphates, which show greater stability than analogues of mononucleotides (Shaver et al., 2005; Yerxa et al., 2002). Indeed, dinucleotides have been successfully developed before as $P2Y_2$-R agonists. Thus, $Up_4U$ (INS365, Diquafosol) and $Up_4dC$ (INS37217, Denufosol) have been clinically tested for the treatment of dry eye disease and cystic fibrosis, respectively, however, both compounds did not show satisfying results at phase 3 clinical trial (http://www.businesswire.com/news/home/20110103005364/en; Jacobson and Boeynaems, 2010).

Ginsburg-Shmuel et al. (2010) discloses 5-OMe-UDP as a $P2Y_6$-receptor agonist. As particularly shown, 5-OMe-UDP adopts the anti-conformation that is favored by the receptors, and the S sugar puckering that is the conformation preferred by the $P2Y_6$-receptors but not the $P2Y_2$- or $P2Y_4$-receptors, and thus fulfills the conformational and H-bonding requirements of $P2Y_6$-receptors and making a potent $P2Y_6$-receptor agonist ($EC_{50}$=0.08 μM vs. 0.14 μM for UDP).

U.S. Pat. No. 7,084,128 discloses a method of reducing IOP by administration of certain mono- or di-nucleotides, preferably mono- or diadenosine, mono-, di-, tri-, tetra-, penta- or hexaphosphate derivatives, or a pharmaceutically-acceptable salt thereof. The particular compounds exemplified are 2'-(O)-,3'-(O)-(benzyl) methylenedioxy-adenosine-5'-triphosphate and 2'-(O)-,3'-(O)-(benzyl)methylene dioxy-2"-(O)-,3"-(O)-benzyl methylene dioxy-$P^1,P^4$-di(adenosine 5'-)tetra phosphate, and as shown, at a concentration of 0.25 mM, these compounds produced a time dependent reduction in IOP, which was maximal at 1-2 hours with a reduction of 21-22%.

Eliahu et al. (2010) discloses certain non-hydrolyzable adenosine di- or triphosphate analogues such as 2MeS-adenosine-β,γ-$CH_2$-5'-triphosphate and 2MeS-adenosine-β,γ-$CCl_2$-5'-triphosphate as potent agents for reducing IOP. As stated in this publication, 2MeS-adenosine-β,γ-$CCl_2$-5'-triphosphate reduced IOP in normotense rabbits by 32% ($EC_{50}$=95.5 nM), wherein the duration of effect was about 5 hours, i.e., was found to be more effective at reducing IOP than several common glaucoma drugs and thus represents a promising alternative to timolol maleate, which cannot be used for the treatment of patients suffering from asthma or cardiac problems.

SUMMARY OF INVENTION

It has now been found, in accordance with the present invention, that certain 5-methoxyuridine nucleotides are capable, upon administration to the cornea, to significantly reduce intraocular pressure (IOP) in male New Zealand white rabbits, and are thus considered promising candidates for treatment of ocular hypertension and/or glaucoma through selective activation of P2Y$_6$ receptors. The particular compound exhibiting the strongest hypotensive effect was one of the two diastereoisomers of 5-methoxyuridine-5'-O-(α-boranodiphosphate), which reduced IOP in normotense rabbits by 45%, more than any drug currently available, wherein the duration of effect was about 4 hours.

In one aspect, the present invention provides a compound of the general formula I:

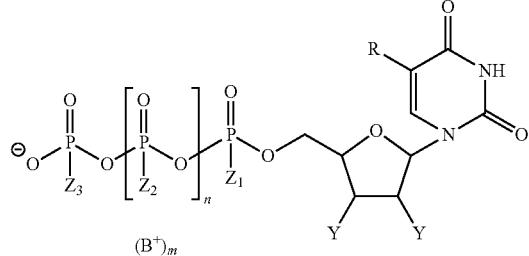

or a diastereoisomer or mixture of diastereoisomers thereof,
wherein
R is —O—($C_1$-$C_8$)alkyl, or —S—($C_1$-$C_8$)alkyl;
Y each independently is H, or —OH;
$Z_1$, $Z_2$ and $Z_3$ each independently is O$^-$, or $BH_3^-$;
n is 0 or 1;
m is 3 or 4; and
B$^+$ represents a pharmaceutically acceptable cation,
  but excluding the compounds wherein $Z_1$, $Z_2$, if present, and $Z_3$ are each O$^-$.

In another aspect, the present invention provides a pharmaceutical composition comprising a compound of the general formula I but excluding the compounds wherein $Z_1$, $Z_2$, if present, and $Z_3$ are each O$^-$, or a diastereoisomer or mixture of diastereoisomers thereof, and a pharmaceutically acceptable carrier or diluent.

In a further aspect, the present invention provides a pharmaceutical composition for reducing intraocular pressure, more particularly, for prevention or treatment of intraocular hypertension and/or glaucoma, comprising a compound of the general formula I, including the compounds wherein $Z_1$, $Z_2$, if present, and $Z_3$ are each O$^-$, or a diastereoisomer or mixture of diastereoisomers thereof, and a pharmaceutically acceptable carrier or diluent.

In still another aspect, the present invention provides a compound of the general formula I, including the compounds wherein $Z_1$, $Z_2$, if present, and $Z_3$ are each O$^-$, or a diastereoisomer or mixture of diastereoisomers thereof, for use in reducing intraocular pressure.

In yet another aspect, the present invention relates to use of a compound of the general formula I, including the compounds wherein $Z_1$, $Z_2$, if present, and $Z_3$ are each O$^-$, or a diastereoisomer or mixture of diastereoisomers thereof, for the preparation of a pharmaceutical composition for reducing intraocular pressure.

In still a further aspect, the present invention relates to a method for reducing intraocular pressure in an individual in need thereof comprising administering to said individual a therapeutically effective amount of a compound of the general formula I, including the compounds wherein $Z_1$, $Z_2$, if present, and $Z_3$ are each O$^-$, or a diastereoisomer or mixture of diastereoisomers thereof.

DETAILED DESCRIPTION OF THE INVENTION

Figure 1:
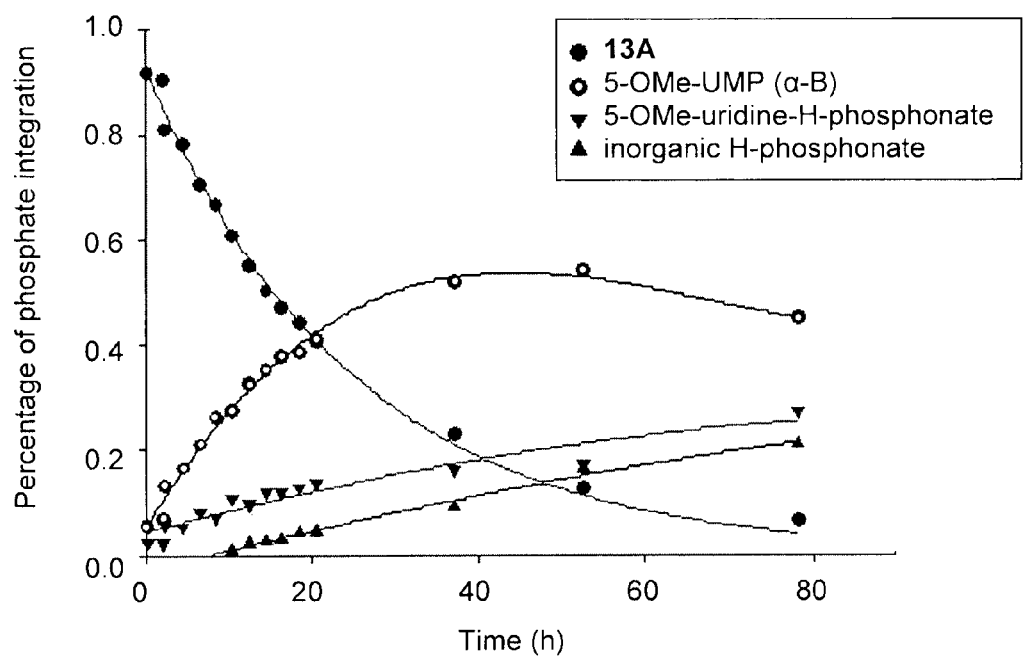
FIG. 1 shows the rate of hydrolysis of 13A at gastric-juice simulating conditions monitored by $^{31}$P NMR at 240 MHz. The different curves represent the species that exist in the solution at different times due to the hydrolysis.

The present invention provides, in one aspect, certain uridine nucleotides of the general formula I as defined above, in which the carbon atom at position 5 of the uracil ring is substituted by —O-alkyl or —S-alkyl, and at least one of the non-bridging oxygen atoms of the di- or tri-phosphate is replaced by a borano group.

The term "($C_1$-$C_8$)alkyl" as used herein typically means a straight or branched hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are ($C_1$-$C_6$)alkyl groups, more preferably ($C_1$-$C_4$)alkyl groups, most preferably methyl and ethyl.

In certain embodiments, the compound of the present invention is a compound of the general formula I, wherein R is —O—($C_1$-$C_8$)alkyl, preferably —O—($C_1$-$C_6$)alkyl, more preferably —O—($C_1$-$C_4$)alkyl, most preferably —OCH$_3$ or —OC$_2$H$_5$.

In certain embodiments, the compound of the present invention is a compound of the general formula I, wherein R is —S—($C_1$-$C_8$)alkyl, —S—($C_1$-$C_6$)alkyl, more preferably —S—($C_1$-$C_4$)alkyl, most preferably —SCH$_3$ or —SC$_2$H$_5$.

In certain embodiments, the compound of the present invention is a compound of the general formula I, wherein n is 0. Such compounds may be uridine diphosphate derivatives, i.e., compounds wherein Y each is OH, as well as deoxy- or dideoxy-uridine diphosphate derivatives, i.e., compounds wherein one or both of the Ys, respectively, is H. Particular such compounds are those comprising (i) a sole borano group at position α, i.e., wherein $Z_1$ is $BH_3^-$, and $Z_3$ is $O^-$; (ii) a sole borano group at position β, i.e., wherein $Z_3$ is $BH_3^-$, and $Z_1$ is $O^-$; or (iii) two borano groups at positions α and β, i.e., wherein $Z_1$ and $Z_3$ are $BH_3^-$.

In certain embodiments, the compound of the present invention is a compound of the general formula I, wherein n is 1. Such compounds may be uridine triphosphate derivatives, i.e., compounds wherein Y each is OH, as well as deoxy- or dideoxy-uridine triphosphate derivatives, i.e., compounds wherein one or both of the Ys, respectively, is H. Particular such compounds are those comprising (i) a sole borano group at position α, i.e., wherein $Z_1$ is $BH_3^-$, and $Z_2$ and $Z_3$ are $O^-$; at position β, i.e., wherein $Z_2$ is $BH_3^-$, and $Z_1$ and $Z_3$ are $O^-$; or at position γ, i.e., wherein $Z_3$ is $BH_3^-$, and $Z_1$ and $Z_2$ are $O^-$; (ii) two borano groups at positions α and β, i.e., wherein $Z_1$ and $Z_2$ are $BH_3^-$, and $Z_3$ is $O^-$; at positions α and γ, i.e., wherein $Z_1$ and $Z_3$ are $BH_3^-$, and $Z_2$ is $O^-$; or at positions β and γ, i.e., wherein $Z_2$ and $Z_3$ are $BH_3^-$, and $Z_1$ is $O^-$; or (iii) three borano groups at positions α, β and γ, i.e., wherein $Z_1$ to $Z_3$ are $BH_3^-$.

In particular embodiments, the compound of the present invention is a compound of the general formula I, wherein R is —O—$(C_1$-$C_4)$alkyl, preferably —$OCH_3$ or —$OC_2H_5$, n is 0, and (i) $Z_1$ is $BH_3^-$, and $Z_3$ is $O^-$; (ii) $Z_1$ is $O^-$, and $Z_3$ is $BH_3^-$; or (iii) $Z_1$ and $Z_3$ are $BH_3^-$.

In other particular embodiments, the compound of the present invention is a compound of the general formula I, wherein R is —O—$(C_1$-$C_4)$alkyl, preferably —$OCH_3$ or $OC_2H_5$, n is 1, and (i) $Z_1$ is $BH_3^-$, and $Z_2$ and $Z_3$ are $O^-$; (ii) $Z_2$ is $BH_3^-$, and $Z_1$ and $Z_3$ are $O^-$; (iii) $Z_3$ is $BH_3^-$, and $Z_1$ and $Z_2$ are $O^-$; (iv) $Z_1$ and $Z_2$ are $BH_3^-$, and $Z_3$ is $O^-$; (v) $Z_1$ and $Z_3$ are $BH_3^-$, and $Z_2$ is $O^-$; (vi) $Z_2$ and $Z_3$ are $BH_3^-$, and $Z_1$ is $O^-$; or (vii) $Z_1$ to $Z_3$ are $BH_3^-$.

The specific uridine nucleotide derivatives of the general formula I described in the specification are herein identified compounds/analogues 12, 13 and 14 in bold, and the specific uridine dinucleotide derivatives described in the specification, not encompassed by the general formula I, are herein identified compounds/analogues 15, 16 and 17 in bold. Compound 12 is also identified by the name 5-methoxyuridine diphosphate (5-OMe-UDP); compound 13 is also identified by the name 5-methoxyuridine-5'-O-(α-boranodiphosphate); compound 14 is also identified by the name 5-methoxyuridine-5'-O-(α-boranotriphosphate); compound 15 is also identified by the name di-(5-OMe)-uridine 5',5"-$P^1$,$P^3$, triphosphate; compound 16 is also identified by the name di-(5-OMe)-uridine 5',5"-$P^1$,$P^3$,α-boranotriphosphate; and compound 17 is also identified by the name di-(5-OMe)-uridine 5"5"-$P^1$,$P^3$,β-boranotriphosphate. In cases a pair of diastereoisomers exist for a certain analogue, such as in the case of analogue 13, those diastereoisomers are herein identified A and B, e.g., analogues/diastereoisomers 13A and 13B. Particular intermediates described in the specification are herein identified by the Arabic numbers 1-7. Uridine-5'-O-(α-boranodiphophate) is herein identified by the Arabic number 11. The chemical structures of all these compounds/analogues are depicted in Appendix A and/or in Scheme 1 hereinafter.

In one specific embodiment, the compound of the present invention is 5-methoxyuridine-5'-O-(α-boranodiphosphate), i.e., a compound of the general formula I, wherein R is —$OCH_3$, n is 0, Y each is —OH, $Z_1$ is $BH_3^-$, and $Z_3$ is $O^-$ (compound 13). A preferred compound is that characterized by being the isomer with a retention time ($R_t$) of 8.97 min when separated from a mixture of diastereoisomers using a semi-preparative reverse-phase Gemini 5μ column (C-18 110 A, 250×10 mm, 5 micron), and isocratic elution [100 mM triethylammonium acetate, pH 7: $CH_3CN$, 94:6] with flow rate of 5 ml/min (compound 13A).

In another specific embodiment, the compound of the present invention is 5-methoxyuridine-5'-O-(α-boranotriphosphate), i.e., a compound of the general formula I, wherein R is —$OCH_3$, n is 1, Y each is —OH, $Z_1$ is $BH_3^-$, and $Z_2$ and $Z_3$ are $O^-$ (compound 14).

The compounds of the general formula I may be synthesized according to any technology or procedure known in the art, e.g., as described in detail in the Examples section hereinafter. The compounds of the invention may have an asymmetric center, e.g., in the Pα, and may accordingly exist as pairs of diastereoisomers. In cases a pair of diastereoisomers exists, the separation and characterization of the different diastereoisomers may be accomplished using any technology known in the art, e.g., using a semi-preparative reverse-phase column and isocratic solution as described in the Examples section.

The compounds of the general formula I are in the form of pharmaceutically acceptable salts.

In certain embodiments, the cation B is an inorganic cation of an alkali metal such as, but not limited to, $Na^+$, $K^+$ and $Li^+$.

In other embodiments, the cation B is ammonium ($NH_4^+$) or is an organic cation derived from an amine of the formula $R_4N^+$, wherein each one of the Rs independently is selected from H, $C_1$-$C_{22}$, preferably $C_1$-$C_6$ alkyl, such as methyl, ethyl, propyl, isopropyl, butyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrolydine, piperidine and morpholine.

In further embodiments, the cation B is a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidylethanolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; fatty acid esters; glycerol esters; sphingolipids; cardiolipin; cerebrosides; ceramides; and mixtures thereof. Neutral lipids also include cholesterol and other 3β hydroxy-sterols. Other neutral lipids contemplated herein include phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols.

Examples of cationic lipid compounds include, without being limited to, Lipofectin® (Life Technologies, Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies, Burlington, Ontario) (3:1 (w/w) formulation of polycationic lipid 2,3-dioleyloxy-N-[2 (spermine-carboxamido)ethyl]-N,N-dimethyl-1-propanamin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation), Metafectene (Biontex, Munich, Germany) (Polycationic lipid), Eu-fectins (Promega Biosciences, San Luis Obispo, Calif.) (ethanolic cationic lipids numbers 1 through 12: $C_{52}H_{106}N_6O_4.4CF_3CO_2H$, $C_{88}H_{178}N_8O_4S_2.4CF_3CO_2H$, $C_{40}H_{84}NO_3P.CF_3CO_2H$, $C_{50}H_{103}N_7O_3.4CF_3CO_2H$, $C_{55}H_{116}N_8O_2.6CF_3CO_2H$, $C_{49}H_{102}N_6O_3.4CF_3CO_2H$, $C_{44}H_{89}N_5O_3.2CF_3CO_2H$, $C_{100}H_{206}N_{12}O_4S_2.8CF_3CO_2H$, $C_{162}H_{330}N_{22}O_9.13CF_3CO_2H$, $C_{43}H_{88}N_4O_2 2CF_3CO_2H$, $C_{43}H_{88}N_4O_3.2CF_3CO_2H$, $C_{41}H_{78}NO_8P$); Cytofectene (Bio-Rad, Hercules, Calif.) (mixture of a cationic lipid and a neutral lipid), GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

As shown in the Examples section hereinafter, analogue 13A is a potent and selective agonist at the $P2Y_6$ receptor, when expressed in 1321N1 astrocytoma cells, and is significantly more potent than both the endogenous agonist UDP and analogue 12 (Ginsburg-Shmuel et al., 2010). The introduction of a chiral center in 5-OMe-UDP by $BH_3$-substitution of the non-bridging oxygen at Pa reveals stereo-specificity of the receptor for the A-isomer over the B-isomer. The A-isomer of the mono-nucleotide derivative 13 was the most potent among the tested nucleotides with $EC_{50}$=0.008 µM, and was more than 500-fold more potent than the corresponding B-isomer ($EC_{50}$=4.3 µM) and 24-fold more potent than the endogenous agonist UDP ($EC_{50}$=0.15 µM). Although borano-substitution dramatically enhanced the potency of analogue 12 at $P2Y_6$-R, the corresponding triphosphate mono-nucleotide 14 was hardly active at the $P2Y_6$-R due to the preference of the receptor for three phosphate negative charges. A stereo-specificity similar to that of analogue 13, although less pronounced, could be observed for the dinucleotide derivative 16, wherein the potency of the A-isomer ($EC_{50}$=0.06 µM) was in the range of that of UDP but only about 40-fold higher than that of the B-isomer ($EC_{50}$=2.2 µM). The non-chiral dinucleotide derivative 17, with a $BH_3$-substituent at the middle phosphate, showed a potency ($EC_{50}$=0.2 µM) similar to that of the standard agonist UDP; and the dinucleotide derivative 15 without a $BH_3$-substitution showed the weakest potency among the tested nucleotides. None of the nucleotides tested was active at the $P2Y_2$- or $P2Y_4$-receptor in 1321N1 cells and at 1321N1 wild type cells.

The therapeutic potential of the new $P2Y_6$-R agonists is related to their chemical stability and their resistance to enzymatic hydrolysis. Therefore, in a further study described herein, the stability of the most potent analogue found, 13A, vs. that of UDP, 11 and 12, under various conditions, was evaluated, and as found: (i) $P_\alpha$ borano substitution reduces the stability of 13A under conditions simulating gastric juice acidity (pH 1.4 and 37° C.). In particular, under those conditions, analogues 13A and 12 displayed a half-life of 16.9 h and 13 days, respectively, and similar results were obtained for 11 and UDP (16.9 h and 12 days, respectively). The reduction of chemical stability is explained by the susceptibility of the P—B bond to acidic hydrolysis, as compared to that of the P—O bond (Nahum and Fischer, 2004), but even so, a half-life of 16.9 h is quite satisfactory for a drug candidate; (ii) $P_\alpha$ borano substitution increases resistance to degradation by NPP1 and NPP3. In particular, 13A was more stable than its non-borano counterparts UDP and 12 in the presence of both NPP1 and NPP3 (at NPP1-15% vs. 50% and 51% hydrolysis, and at NPP3-28% vs. 45% and 36% hydrolysis, respectively), indicating that the introduction of the boranophosphate moiety at $P_\alpha$ plays an important role in protecting UDP analogues against NPP1,3 hydrolysis. In fact, although the enzymatic degradation by NPP occurs between $P_\alpha$ and $P_\beta$, it is postulated that the $BH_3$ group in analogue 13A, which is larger than O in the parent compound, prevents attack by an essential water molecule on $P_\alpha$ and thus makes these analogues poor NPP substrates. Furthermore, analogue 12 bearing only a modification at the uracil ring was hydrolyzed more slowly by NPP3 but not by NPP1 as compared to UDP; (iii) The $BH_3$ substitution at $P_\alpha$ position and OMe at the C5 position of uracil nucleotides increase resistance to degradation in human blood serum. As particularly shown, 12 bearing a methoxy group at C5 of the uracil ring was more stable than UDP (half-life of 11.9 h vs. 2.4 h), and 13A, bearing both $BH_3$ and methoxy groups, displayed even greater stability with a half-life of 17 h. Similar results were obtained for uridine-5'-O-(α-boranodiphosphate) ($t_{1/2}$=21 h). It is suggested that the methoxy group presents a steric hindrance which causes analogue 12 to be a poor substrate for the various enzymes present in blood serum. Apparently, the borano group in 13A and 11 renders the nucleotides even more stable to enzymatic degradation than UDP.

As further shown in the Examples section, analogue 12 reduced IOP in normotense rabbits by 31%, and analogue 13A reduced IOP in normotense rabbits by 45%, more than any marketed drug, e.g., Xalatan®, Trusopt®, and Pilocarpine, wherein the duration of action was about 4 h.

In another aspect, the present invention thus provides a pharmaceutical composition comprising a compound of the general formula I but excluding the compounds wherein $Z_1$, $Z_2$, if present, and $Z_3$ are each O⁻, or a diastereoisomer or mixture of diastereoisomers thereof, and a pharmaceutically acceptable carrier or diluent.

In a further aspect, the present invention provides a pharmaceutical composition for reducing, i.e., lowering, intraocular pressure, more particularly, for prevention or treatment of intraocular hypertension and/or glaucoma, comprising a compound of the general formula I, including the compounds wherein $Z_1$, $Z_2$, if present, and $Z_3$ are each O⁻, or a diastereoisomer or mixture of diastereoisomers thereof, and a pharmaceutically acceptable carrier or diluent.

In particular embodiments, the compound comprised within this composition is 5-methoxyuridine diphosphate, i.e., a compound of the general formula I wherein R is —$OCH_3$, n is 0, Y each is —OH, and $Z_1$ and $Z_3$ are O⁻ (12), compound 13, more particularly 13A, or compound 14, preferably compound 13A.

The terms "intraocular hypertension", "ocular hypertension", or "intraocular pressure", as used herein interchangeably, refer to an intraocular pressure in an eye of a patient that is above a normal level and is correlated as a risk factor for the development of visual field loss and glaucoma.

Glaucoma is a heterogeneous group of optic neuropathies that share certain clinical features, wherein the loss of vision is due to the selective death of retinal ganglion cells in the neural retina that is clinically diagnosed by characteristic changes in the visual field, nerve fiber layer defects, and a progressive cupping of the optic nerve head (ONH). One of the main risk factors for the development of glaucoma is the presence of intraocular hypertension (elevated intraocular pressure, IOP). IOP also appears to be involved in the pathogenesis of normal tension glaucoma where patients have what is often considered to be normal IOP. The elevated IOP associated with glaucoma is due to elevated aqueous humor outflow resistance in the trabecular meshwork (TM), a small-specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous ONH. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

The term "glaucoma" as used herein is a disease of the eye characterized by increased pressure inside the eye with resultant optic nerve damage. Glaucoma includes, but is not limited to, primary glaucoma, secondary glaucoma, juvenile glaucoma, congenital glaucoma, pseudoexfoliation glaucoma, acute angle closure glaucoma, absolute glaucoma, chronic glaucoma, narrow angle glaucoma, chronic open angle glaucoma, simplex glaucoma and familial glaucomas, including, without limitation, pigmentary glaucoma, high tension glaucoma, and low tension glaucoma and their related diseases.

The pharmaceutical compositions of the invention can be formulated for any suitable route of administration, e.g., intravenous, intraarterial, intramuscular, subcutaneous or intraperitoneal administration. Nevertheless, when used for reducing intraocular pressure, more particularly, for prevention or treatment of intraocular hypertension and/or glaucoma, the compositions are formulated as ophthalmic compositions, e.g., ophthalmic drops, emulsion, suspension, gel, ointment, or membranous ocular eye patches.

The ophthalmic compositions of the present invention can be provided in a variety of formulations and dosages. These compositions may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the compound of the general formula I, into association with a liquid carrier, a finely divided solid carrier, or both, and then, if necessary, shaping the product into the desired formulation.

The ophthalmic compositions of the invention, intended for direct application to the eye, may be formulated so as to have both pH and tonicity compatible with the eye. This will normally require a buffer to maintain the pH of the composition at or near physiologic pH, i.e., in the range of 5-9, preferably 6 to 8, more preferably 6.8-7.4; and may further require a tonicity agent to bring the osmolality of the composition to a level at or near 210-320 milliosmoles per kilogram (mOsm/kg). In certain embodiments, the composition of the invention has an osmolality in the range of 50-700 mOsm/kg, preferably 100-600 mOsm/kg, more preferably 150-500 mOsm/kg, still more preferably 200-400 mOsm/kg, most preferably 200-350 mOsm/kg.

The ophthalmic compositions of the invention may be administered to the eye of the subject by any suitable means. In one embodiment, the composition is in the form of a liquid, emulsion, gel or suspension of the compound of the general formula I, and it is administered as drops, spray, or gel. In another embodiment, the active agent, i.e., the compound of the general formula I, is applied to the eye via liposomes. In a further embodiment, the active agent is contained within a continuous or selective-release device, e.g., membranes such as, but not limited to, those employed in the Ocusert™ System (Alza Corp., Palo Alto, Calif.).

In one embodiment, the active agent can be contained within, carried by, or attached to contact lenses, which are placed on the eye. In other embodiments, the active agent is contained within a swab or sponge, or within a liquid spray, which is applied to the ocular surface. In a further embodiment, the active agent is directly injected into the ocular tissues, e.g., by subconjunctival, subscleral, or intravitreal injection, or onto the eye surface.

In addition to the active agent, the ophthalmic compositions of the present invention contain a physiologically compatible carrier or vehicle as those skilled in the ophthalmic art can select using conventional criteria. Such vehicles may be selected from known ophthalmic vehicles that include, inter alia, saline solution, water, polyethers such as polyethylene glycol, polyvinyls such as polyvinyl alcohol and povidone, cellulose derivatives such as methylcellulose and hydroxypropyl methylcellulose, cyclodextrins, in particular betahydroxypropyl cyclodextrin, petroleum derivatives, e.g., mineral oil and white petrolatum, animal fats such as lanolin, polymers of acrylic acid such as carboxypolymethylene gel, vegetable fats such as peanut oil, polysaccharides such as dextrans, an alginate such as sodium alginate optionally comprising guluronic acid and/or mannuronic acid, glycosaminoglycans such as sodium hyaluronate, and salts such as sodium chloride and potassium chloride.

The optimal dosage for administration will depend on the state of the patient, and will be determined as deemed appropriate by the practitioner. In particular, compositions for the treatment of glaucoma may be administered daily, twice daily, or 3-4 times daily, and/or upon the occurrence of symptoms associated with the condition; and over a period of time consistent with treatment of the ocular hypertension and glaucoma, e.g., for a period of weeks, months, years, or decades.

In still another aspect, the present invention provides a compound of the general formula I, including the compounds wherein $Z_1$, $Z_2$, if present, and $Z_3$ are each O$^-$, or a diastereoisomer or mixture of diastereoisomers thereof, for use in reducing intraocular pressure. In particular embodiments, the compound used according to the invention is compound 12, 13, more particularly 13A, or 14, preferably compound 13A.

In yet another aspect, the present invention relates to use of a compound of the general formula I, including the compounds wherein $Z_1$, $Z_2$, if present, and $Z_3$ are each O$^-$, or a diastereoisomer or mixture of diastereoisomers thereof, for the preparation of a pharmaceutical composition, in particular, an ophthalmic composition, for reducing intraocular pressure. In particular embodiments, the compound used according to the invention is compound 12, 13, more particularly 13A, or 14, preferably compound 13A.

In still a further aspect, the present invention relates to a method for reducing intraocular pressure in an individual in need thereof comprising administering to said individual a therapeutically effective amount of a compound of the general formula I, including the compounds wherein $Z_1$, $Z_2$, if present, and $Z_3$ are each O$^-$, or a diastereomer or mixture of diastereoisomers thereof. In particular embodiments, the compound used according to the method of the invention is compound 12, 13, more particularly 13A, or 14, preferably compound 13A.

The invention will now be illustrated by the following non-limiting Examples.

EXAMPLES

Materials and Methods

General

All air and moisture sensitive reactions were carried out in flame-dried, argon flushed, two-neck flasks sealed with rubber septa. All reactants in moisture sensitive reactions were dried overnight in a vacuum oven, and the reagents were introduced by syringe. Progress of reactions was monitored by TLC on precoated Merck silica gel plates (60E-254). Visualization was accomplished by UV light. Flash chromatography was carried out on silica gel (Davisil Art. 1000101501). All commercial reagents were used without further purification, unless otherwise noted. All phosphorylation reactions were carried out in flame-dried, argon-flushed, two-neck flasks sealed with rubber septa. Nucleosides were dried in-vacuo overnight. Proton Sponge® was kept in a desiccator. Phosphorus oxychloride was distilled and kept under nitrogen. Bpi was prepared according to literature. (Nahum and Fisher, 2004). Tri-n-butylammonium pyrophosphate solution were prepared as described previously. The preparation of the tri-n-butylammonium-tri-n-octylammonium and the bis(trioctylammonium) 5'-monophosphate 5-OMe-uridine salts were achieved by eluting the uridine nucleotide derivative (obtained after LC separation) through an activated Dowex-H+-form using deionized water to an ice-cooled EtOH solution containing 1 eq. tri-n-octylamine and 1 eq. tri-n-butylamine. The preparation of the tetra-n-butylammonium 5'-diphosphate 5-OMe-uridine salt was achieved by eluting the uridine nucleotide derivative (obtained after LC separation) through a CM Sephadex previously washed with an excess of tetrabutylammonium aquase solution. 5-Methoxy uracil, 5-methoxyuridine, 1, and 2',3'-O-methoxymethylidene-5-OMe-uridine, 2, were prepared according to literature (Stout and Robins, 1972; Chesterfield et al., 1960; Niedballa and Vorbruggen, 1976; Griffin et al., 1967). 5-OMe-UMP and 5-OMe-UDP, 12, were prepared as previously described (Niedballa and Vorbruggen, 1976). pH measurements were performed with a Metrohm pH electrode and a Metrohm 827 pH lab pH meter. Compounds were characterized by NMR using Bruker AC-200, DPX-300, or DMX-600 spectrometers. $^1$H NMR spectra were recorded at 200, 300, or 600 MHz. Chemical shifts are expressed in ppm downfield from Me$_4$Si (TMS), used as an internal standard. Nucleotides were characterized also by $^{31}$P NMR in D$_2$O, using 85% H$_3$PO$_4$ as an external reference on Bruker AC-200 and DMX-600 spectrometers. High resolution mass spectra were recorded on an AutoSpec Premier (Waters UK) spectrometer by chemical ionization. Nucleotides were analyzed under ESI (electron spray ionization) conditions on a Q-TOF microinstrument (Waters, UK). Primary purification of the nucleotides was achieved on a LC (Isco UA-6) system using a Sephadex DEAE-A25 column, swollen in 1M NaHCO$_3$ at room temperature for 1 day. The resin was washed with deionized water before use. The LC separation was monitored by UV detection at 280 nm A buffer gradient of NH$_4$HCO$_3$ was applied as detailed below. Final purification of the nucleotides was achieved on an HPLC (Hitachi Elite LaChrome) system, using a semi-preparative reverse-phase column (Gemini 5µ C-18 110A, 250×10.00 mm, 5 micron, Phenomenex, Torrance, USA). The purity of the nucleotides was evaluated with an analytical reverse-phase column system (Gemini 5µ C-18 110A, 150 mm×4.60 mm; 5 µm; Phenomenex, Torrance, Calif.) using two solvent systems: solvent system I, (A) 100 mM triethylammonium acetate (TEAA), pH 7:(B) CH$_3$CN; solvent system II, (A) 10 mM PBS buffer, pH 7.4:(B) CH$_3$CN. The details of the solvent system conditions used for the separation of each product are given below. The purity of the nucleotides was generally ≥95%.

Stability Assays

For the chemical stability assays, $^{31}$P NMR spectra were recorded (isotope frequency of 240 MHz). NPP 1 and 3 enzymes were provided by the Center of Research in Rheumatology and Immunology, Laval University (Québec, Canada). Human blood serum was obtained from a blood bank (Tel-Hashomer Hospital, Israel). All stability experiments were performed in duplicates.

Evaluation of Activity of Analogues 13A/B, 15, 16 and 17 at P2Y$_{2/4/6}$ Receptors Cell Culture and Transfection.

Green fluorescent protein (GFP) constructs of human P2Y$_2$-R, P2Y$_4$-R and P2Y$_6$-R were expressed in 1321N1 astrocytoma cells, which lack endogenous expression of P2X- and P2Y-receptors. The respective cDNA of the receptor gene was cloned into a pEGFPN1 vector. After transfection using FuGENE 6 Transfection Reagent (Roche Molecular Biochemicals, Mannheim, Germany), the cells were selected with 0.5 mg/ml G418 (geneticine; Merck Chemicals, Darmstadt, Germany) and grown in Dulbecco's modified Eagles' medium (DMEM) supplemented with 10% fetal calf serum, 100 U/ml penicillin and 100 U/ml streptomycin at 37° C. and 5% CO$_2$. The expression and cell membrane localization of the respective P2Y receptors was confirmed through the analysis of the GFP fluorescence. The functionality of the expressed GFP-labeled receptor in cells was verified by recording a change of $[Ca^{2+}]_i$ after stimulation with the appropriate receptor agonist.

Single Cell $[Ca^{2+}]$ Measurements.

1321N1 astrocytoma cells transfected with the respective plasmid for P2YR-GFP expression plated on coverslips (22 mm diameter) and grown to approximately 80% density were incubated with 2 µM fura 2/AM and 0.02% pluronic acid in Na-HBS buffer (Hepes buffered saline: 145 mM NaCl, 5.4 mM KCl, 1.8 mM CaCl$_2$, 1 mM MgCl$_2$, 25 mM glucose, 20 mM Hepes/Tris pH 7.4) for 30 min at 37° C. The cells were superfused (1 ml/min, 37° C.) with different concentrations of nucleotide in Na-HBS buffer, and the nucleotide-induced change of $[Ca^{2+}]_i$ was measured by detecting the respective emission intensity of fura 2/AM at 510 nm with after 340 nm and 380 nm excitations (Ubl et al., 1998). The average maximal amplitude of the responses and the respective standard errors were calculated from the ratio of the fura 2/AM fluorescence intensities with excitations at 340 nm and 380 nm (only MT-labeled cells were analysed). Microsoft Excel (Microsoft Corp., Redmond, Wash., USA) and SigmaPlot (SPSS Inc., Chicago, Ill., USA) were used to derive the concentration-response curves and EC$_{50}$ values from the average response amplitudes obtained in at least three independent experiments (Ecke et al., 2006, 2008). Only cells with a clear MT-signal and with the typical calcium response kinetics upon agonist pulse application were included in the data analysis. The GFP-tagged P2Y receptors are suitable for pharmacological and physiological studies, as previously reported (Tulapurkar et al., 2004, 2006; Zylberg et al., 2007).

Evaluation of Activity of Analogues 14A/B at P2Y$_{2/4/6}$ Receptors

Cell Culture.

1321N1 cell lines stably expressing the human P2Y$_6$ receptors were grown as previously described in DMEM (5% FBS, 100 IU/ml penicillin, 100 µg/ml streptomycin, 1× Glutamax, 10 mM Hepes and 0.5 mg/ml G-418) at 37° C. in a humidified atmosphere containing 5% CO$_2$ and 95% air (Gendron et al., 2003).

Cytosolic $[Ca^{2+}]$ Measurement.

1321N1 cells (10×10$^6$ cells grown in 10 cm$^2$ dishes) were harvested by a brief trypsin/EDTA treatment, suspended in complete culture medium, and washed by centrifugation for 3 min at 100×g before being incubated with 1 µM Fluo 4/AM in 4.5 ml HBSS with Ca$^{2+}$ and Mg$^{2+}$ (Wisent, St. Bruno, QC) for 25 min at 37° C. Cells were washed by centrifugation (100×g, 3 min), suspended in HBSS containing Ca$^{2+}$ and Mg$^{2+}$, and incubated for 25 min at 37° C. Cells were washed and suspended in 16 ml of FIBSS containing $Ca^+$ and $Mg^{2+}$. Cell suspension (2 ml) was gently stirred in a quartz cuvette while $[Ca^{2+}]_i$ and monitored on a RF-5301 PC Shimadzu spectrofluorometer with Panormama fluorescence 1.1 software (Man-Tech, Guelph, ON). Excitation wavelengths of 488 nm and emission wavelength of 520 nm were used to measure changes in intracellular Fluo 4 fluorescence intensity (F). At the end of each recording, maximal fluorescence (Fmax) and minimal fluorescence (Fmin) were determined by adding successively 0.1% Triton X-100 and 50 mM EDTA to cell suspensions. The following equation from Grynkiewicz et al. (1985) was used to relate the fluorescence intensity to $Ca^{2+}$ levels: $[Ca^{2+}]=Kd\times(F-Fmin)/(Fmax-F)$, wherein Kd is the $Ca^+$ dissociation constant of the indicator (345 nM).

Animals

Twenty-four male New Zealand white rabbits (2.5±0.5 kg) were kept in individual cages with free access to food and water on controlled 12 h/12 h light/dark cycles. All the protocols used adhere to the Association for Research in Vision and Ophthalmology (ARVO) Statement for the Use of Animals in Ophthalmology and Vision Research and also are in accordance with the European Communities Council Directive (86/609/EEC).

Intraocular Pressure Measurements

Intraocular pressure (IOP) was measured by means of a TonoVET rebound tonometer supplied by Tiolat Oy (Helsinki, Finland). The application of this tonometer to animals does not require the use of any anaesthetic. For single dose experiments, different analogues were applied unilaterally to the cornea at a concentration of 100 μM and a fixed volume of 10 μl. The contralateral eye received the same volume of saline solution (0.9% NaCl, vehicle). Two IOP measurements were taken before any analogue was instilled. Experiments were performed following a blinded design where no visible indication was given to the experimenter as to the nature of the applied solution. IOP was followed up to 8 h to study the time course of the effect. Some of the analogues were assayed over a range of doses from 1 nM to 100 μM to generate dose-response curves. For these experiments, KV was measured as the maximal response obtained with each dose of the analogue. Dose-response curves were calculated by plotting the IOP value for given concentration versus that concentration (from 1 nM to 100 μM). pD2 values were obtained by fitting the values to a dose-response-curve equation according to ORIGIN8.0 software. With the pD2 value it was possible to calculate the $EC_{50}$ by multiplying by −1 and then take the antilogarithm. The obtained value is the $EC_{50}$ expressed in molar concentration. In all experiments, on any given day, only a single dose was tested on a single animal, which was washed out at least 2 days between doses. The commercial hypotensive agents, Xalatan® (latanoprost; 0.005%), Trusopt® (dorzolamide hydrochloride (2%), and Pilocarpine were assayed by applying a volume of 40 μl.

Statistical Analysis

All data are presented as the means±s.e.m. Significant differences were determined by two-tailed Student's t-tests. The plotting and fitting of dose-response curves was carried out with Microcal Origin v. 7.0 software (Microcal Software, U.S.A).

Example 1

Synthesis of 5-OMe-uridine-5'-O-(α-boranodiphosphate), 13

Synthesis of 5-methoxyuridine, 1

5-methoxyuridine, 1, was synthesized as previously described (Stout and Robins, 1972; Chesterfield et al., 1960; Niedballa and Vorbruggen, 1976), and was used, e.g., for the preparation of 5-OMe-UDP, 12, as previously described (Ginsburg-Shmuel et al., 2010).

Synthesis of 2',3'-O-methoxymethylidene-5-OMe-uridine, 2

The protected nucleoside, 2, was synthesized as previously described (Griffin et al., 1967). In particular, a suspension of 5-OMe-uridine, 1, (300 mg, 1.09 mmol) and p-TsOH (catalytic amount) in trimethyl orthoformate (1.09 ml, 9.85 mmol, 9 eq) was prepared in a flamed-dried, nitrogen-flushed two-necked round bottom flask, and stirred at room temperature (RT). After 24 h, the solution became almost clear and TLC ($CHCl_3$:MeOH 8:2) showed two less polar spots and the complete disappearance of the starting material. Dowex (weak base) was added (0.31 gr, 1.09 mmol, 1 eq) and the mixture was stirred at RT for 3 h. The liquid was decanted and the MeOH was used for washes. The solution was evaporated to give an oil-like residue. Co evaporations with ether were done and a white solid was obtained (a mixture of two diastereomers: 331.8 mg, 96.3%).

Characterization of 2.

$^1$H-NMR (DMSO-$d_6$, 300 MHz): δ 11.54 (bs, 1H, NH), 7.46, 7.44 (2s, 1H, H-6), 6.101, 6.01 (2s, 1H, CH—$OCH_3$), 6.00, 5.86 (2d, J=2.9 Hz, and J=2.7 Hz, H-1', 1H), 5.21, 5.17 (2m, 1H, OH-5'), 4.99-5.05 (m, 2H, H-2'), 4.88, 4.82 (2dd, J=6.6, 3.4 Hz and J=7.6, 3.8 Hz, 1H, H-3'), 4.18 and 4.09 (2m, 1H, H-4'), 3.58-3.66 (m, 2H, H-5' and H-5"), 3.606 (s, 3H, C—$OCH_3$), 3.30, 3.21 (2s, 3H, CH—$OCH_3$) ppm. HR MALDI (positive) calcd for $C_{12}H_{16}N_2Na_1O_8$ 339.080 found 339.080.

Synthesis of Analogue 13

As depicted in Scheme 1 hereinafter, a solution of 2',3'-O-methoxymethylidene 5-OMe-uridine, 2 (327.1 mg, 1.03 mmol) in dry DMF (2 ml) was prepared in a flame-dried, argon flushed, two-neck flask. Dry pyridine (0.42 ml, 5.17 mmol, 5 eq) and a solution of 2-Cl-1,3,2-benzdioxaphosphorin-4-one (230.4 mg, 1.14 mmol, 1.1 eq) in dry dioxane (2 ml) were added and the solution was stirred at RT for 10 min. Then, a mixture of 1 M $(Bu_3NH^+)_2P_2O_7H_2^{-2}$ in DMF (1.55 ml, 1.55 mml, 1.5 eq) and $Bu_3N$ (0.99 ml, 4.14 mmol, 4 eq) was added and the solution turned turbid and then clear again. Then, a 2 M solution of $BH_3$—$SMe_2$ complex in THF (5.17 ml, 10.34 mmol, 10 eq) was added. After 15 min, ethylene diamine (0.35 ml, 5.17 mmol, 5 eq) was added and a white precipitate was formed. After an hour at RT, the reaction was quenched with distilled water (1.4 ml) and the clear solution was evaporated and freeze-dried. TLC (isopropanol: 25% $NH_4OH$: $H_2O$ 11:2:7) of the crude material showed a main polar product ($R_f$=0.35). The methoxymethylidene protecting group was removed by acidic hydrolysis (10% HCL solution was added until pH 2.3 was obtained). After 3 h at RT, the pH was rapidly raised to 9 by addition of 24% $NH_4OH$ solution (pH 11), and the solution was stirred at RT for 45 min and then freeze-dried. The semisolid obtained after freeze-drying was chromatographed on an activated Sephadex DEAE-A25 column. The resin was washed with deionized water and loaded with the crude reaction residue dissolved in a minimal volume of water. The separation was monitored by UV detection (ISCO, UA-6) at 280 nm. A buffer gradient of 0-0.2 M $NH_4HCO_3$ (200 ml of each solution) followed by a second buffer gradient of 0.2-0.4 M $NH_4HCO_3$ (200 ml of each solution) were applied. The different fractions were pooled and freeze-dried three times to yield a white solid. Final separation of the diastereomers and purification of the relevant fractions was carried out on an HPLC system, using a semi-preparative reverse-phase column, under the conditions described bellow. The purity of the nucleotides was evaluated on an analytical reverse-phase column system, in two solvent systems as described below. Finally, aqueous solutions of the products were passed through a Dowex 50WX8-200 ion-exchange resin $Na^+$-form column and the products were eluted with deionized water to obtain the corresponding sodium salts after freeze-drying.

Separation of Diastereoisomers 13A and 13B

The separation of analogue 13 diastereoisomers, 13A and 13B, was accomplished using a semipreparative reverse-phase Gemini 5μ column and isocratic elution with 94:6 (A) 100 mM TEAA, pH 7:(B) $CH_3CN$ at a flow rate of 5 ml/min. Fractions containing purified isomers [$R_t$=8.97 min (13A); 13.45 min (13B isomer)] were collected and freeze-dried. Excess buffer was removed by repeated freeze-drying cycles, with the solid residue dissolved each time in deionized water. Diastereoisomers 13A and 13B were obtained at 50.9% overall yield (253.5 mg) after LC separation.

Characterization of 13A $^1$H NMR ($D_2O$; 600 MHz): δ 7.41 (s, 1H, H-6), 6.00 (d, J=5.6, 1H, H-1'), 4.47 (t, J=5.5, 1H, H-3'), 4.42 (t, J=4.7, 1H, H-3'), 4.32 (m, 1H, H-4'), 4.28 (m, 1H, H-5'), 4.10 (m, 1H, H-5"), 3.83 (s, 3H, $CH_3$), 0.39 (m, 3H, $BH_3$) ppm. $^{31}$P NMR (240 MHz, $D_2O$) δ: 80.43 (m, 1P, $P_α$—$BH_3$), −7.16 (d, J=29.48 Hz, 1P, $P_β$) ppm. HR MALDI (negative) calcd for $C_{10}H_{18}B_1N_2O_{12}P_2$ 431.042 found 431.043. Purity data obtained on an analytical column: retention time: 3.88 min (94.48% purity) using solvent system I isocratic elution of 95:5 A:B over 10 min followed by a gradient from 95:5 to 85:15 over 2 min at a flow rate of 1 ml/min. Retention time: 2.71 min (95.31% purity) isocratic elution of 97.5:2.5 A:B over 8 min followed by a gradient from 97.5:2.5 to 85:15 over 2 min at a flow rate of 1 ml/min.

Characterization of 13B $^1$H NMR ($D_2O$; 600 MHz): δ 7.41 (s, 1H, H-6), 6.02 (d, J=5.8, 1H, H-1'), 4.44 (m, 2H, H-3', H-2'), 4.27 (m, 2H, H-4', H-5'), 4.11 (m, 1H, H-5'), 3.83 (s, 3H, $CH_3$), 0.39 (m, 3H, $BH_3$) ppm. $^{31}$P NMR (240 MHz, $D_2O$) δ: 80.83 (m, 1P, $P_α$—$BH_3$), −7.51 (d, J=32.4 Hz, 1P, $P_β$) ppm. HR MALDI (negative) calcd for $C_{10}H_{18}B_1N_2O_{12}P_2$ 431.042 found 431.043. Purity data obtained on an analytical column: retention time: 6.06 min (95.40% purity) using solvent system I isocratic elution of 95:5 A:B over 10 min followed by a gradient from 95:5 to 85:15 over 2 min at a flow rate of 1 ml/min. Retention time: 4.21 min (95.08% purity) isocratic elution of 99.5:0.5 A:B over 8 min followed by a gradient from 99.5:0.5 to 85:15 over 2 min at a flow rate of 1 ml/min.

Example 2

Synthesis of 5-OMe-uridine-5'-O-(α-boranotriphosphate), 14

5-OMe-uridine-5'-O-(α-boranotriphosphate), 14, was obtained as a by-product from the synthesis of 13 depicted in Scheme 1. After LC separation, the relevant fractions were pooled and freeze-dried three times to yield a white solid. Final separation of the diastereomers and purification of the relevant fractions was carried out on an HPLC system, using a semi-preparative reverse-phase column, under the conditions described below. The purity of the nucleotides was evaluated on an analytical reverse-phase column system, in two solvent systems as described below. Finally, aqueous solutions of the products were passed through a Dowex 50WX8-200 ion-exchange resin $Na^+$-form column and the products were eluted with deionized water to obtain the corresponding sodium salts after freeze-drying.

Separation of Diastereoisomers 14A and 14B

The separation of analogue 14 diastereoisomers, 14A and 14B, was accomplished using a semipreparative reverse-phase Gemini 5μ column and isocratic elution with 93:7 (A) 100 mM TEAA, pH 7:(B) $CH_3CN$ at a flow rate of 5 mL/min. Fractions containing purified isomers [Rt 6.15 min (14A); 9.22 min (14B) isomer)] were collected and freeze-dried. Excess buffer was removed by repeated freeze-drying cycles, with the solid residue dissolved each time in deionized water. Diastereoisomers 14A and 14B were obtained in 8.66% overall yield (51.7 mg) after LC separation.

Characterization of 14A $^1$H NMR ($D_2O$; 200 MHz): δ 7.32 (s, 1H, H-6), 6.00 (d, J=5.5, 1H, H-1'), 4.38 (m, 2H, H-2', H-3'), 4.26 (m, 2H, H-4', H-5'), 4.08 (m, 1H, H-5"), 3.78 (s, 3H, $CH_3$), 0.39 (m, 3H, $BH_3$) ppm. $^{31}$P NMR (81 MHz, $D_2O$) δ: 84.51 (m, 1P, $P_α$—$BH_3$), −10.33 (d, J=19.8 Hz, 1P, $P_γ$), −22.48 (dd, J=29.4, 19.8 Hz, 1P, $P_β$) ppm. HR MALDI (negative) calcd for $C_{10}H_{19}BN_2O_{15}P_3$ 511.009 found 511.008. Purity data obtained on an analytical column: retention time: 4.43 min (94.32% purity) using solvent system I isocratic elution of 93:7 A:B over 10 min followed by a gradient from 93:7 to 85:15 over 2 min at a flow rate of 1 mL/min. Retention time: 3.27 min (94.11% purity) isocratic elution of 97.5:2.5 A:B over 8 min followed by a gradient from 97.5:2.5 to 85:15 over 2 min at a flow rate of 1 mL/min.

Characterization of 14B $^1$H NMR ($D_2O$; 200 MHz): δ 7.32 (s, 1H, H-6), 6.00 (d, J=6.1, 1H, H-1'), 4.38 (m, 2H, H-2', H-3'), 4.24 (m, 2H, H-4', H-5'), 4.10 (m, 1H, H-5"), 3.78 (s, 3H, $CH_3$), 0.37 (m, 3H, $BH_3$) ppm. $^{31}$P NMR (81 MHz, $D_2O$) δ: 84.58 (m, 1P, $P_α$—$BH_3$), −10.20 (d, J=19.5 Hz, 1P, $P_γ$), −22.46 (dd, J=33.3, 19.5 Hz, 1P, $P_β$) ppm. Purity data obtained on an analytical column: retention time: 6.75 min (96.85% purity) using solvent system I isocratic elution of 93:7 A:B over 10 min followed by a gradient from 93:7 to 85:15 over 2 min at a flow rate of 1 mL/min. Retention time: 4.82 min (95.33% purity) isocratic elution of 97.5:2.5 A:B over 8 min followed by a gradient from 97.5:2.5 to 85:15 over 2 min at a flow rate of 1 mL/min.

Example 3

Synthesis of di-(5-OMe)-uridine 5',5"-$P^1$,$P^3$, triphosphate, 15

The tri-n-butylammonium-tri-n-octylammonium 5-OMe-uridine mono phosphate salt (160.8 mg, 0.18 mmol) was dissolved in dry DMF (0.7 ml), and added to a flamed-dried, nitrogen-flushed two-necked round bottom flask containing CDI (145.8 mg, 0.9 mmol, 5 eq). The reaction was stirred at RT. After 2 h TLC (isopropanol: 25% $NH_4OH$: $H_2O$ 11:2:7) showed the presence of a less polar product ($R_f$=0.62) and the complete disappearance of the starting material ($R_f$=0.35). MeOH (0.06 ml, 1.62 mmol, 9 eq) was added to destroy CDI leftovers, and after 10 min, a solution of the tetra-n-butylammonium 5-OMe-uridine diphosphate, 12, (0.18 mmol, 1 eq) in dry DMF (0.5 ml) and $MgCl_2$ (68.4 mg, 0.72 mmol, 4 eq) were added. The solution was stirred at RT and TLC monitoring after 24 hours showed the presence of a more polar product ($R_f$=0.39) and the complete disappearance of the intermediate. The solution was freeze-dried after the addition of water. The semisolid obtained after freeze-drying was chromatographed on an activated Sephadex DEAL-A25 column. The resin was washed with deionized water and loaded with the crude reaction residue dissolved in a minimal volume of water. The separation was monitored by UV detection (ISCO, UA-6) at 280 nm. A buffer gradient of 0-0.2 M $NH_4HCO_3$ (250 ml of each solution) followed by a second buffer gradient of 0.2-0.4 M $NH_4HCO_3$ (300 ml of each solution) were applied. The different fractions were pooled and freeze-dried three times to yield a white solid. Final purification of the relevant fractions was carried out on an HPLC system, using a semi-preparative reverse-phase column, under the conditions described below. The purity of the nucleotides was evaluated on an analytical reverse-phase column system, in two solvent systems as described below. Finally, aqueous solutions of the products were passed through a Dowex 50WX8-200 ion-exchange resin $Na^+$-form column and the products were eluted with deionized water to obtain the corresponding sodium salts after freeze-drying.

Purification of 15

The purification of analogue 15 was accomplished using a semipreparative reverse-phase Gemini 5μ column and isocratic elution with 96:4 (A) 100 mM TEAA, pH 7:(B) $CH_3CN$ at a flow rate of 5 ml/min. The fraction containing the purified analogues ($R_f$=11.3 min) was collected and freeze-dried. Excess buffer was removed by repeated freeze-drying cycles, with the solid residue dissolved each time in deionized water. Analogue 15 was obtained at 51.8% overall yield (76.6 mg) after LC separation.

Characterization of 15

$^1$H NMR ($D_2O$; 600 MHz): δ 7.31 (s, 2H, H-6), 5.90 (d, J=5.2, 2H, H-1'), 4.38-4.40 (m, 4H, H-2, H-3), 4.21-4.25 (m, 6H, H-4'H-5', H-5"), 3.79 (s, 6H, $CH_3$) ppm. $^{31}$P NMR (240 MHz, $D_2O$) δ: −0.89 (d, J=18.0 Hz, 1P, $P_α$), −22.26 (dd, J=18.0, J=18.3 Hz, 1P, $P_β$) ppm. HR MALDI (negative) calcd for $C_{20}H_{28}N_4O_{22}P_3$ 769.041 found 769.045. Purity data obtained on an analytical column: retention time: 3.72 min (97.21% purity) using solvent system I isocratic elution of 96:4 A:B over 10 min followed by a gradient from 96:4 to 85:15 over 2 min at a flow rate of 1 ml/min. Retention time: 2.47 min (97.35% purity) isocratic elution of 99.5:0.5 A:B over 8 min followed by a gradient from 99.5:0.5 to 85:15 over 2 min at a flow rate of 1 ml/min.

Example 4

Synthesis of di-(5-OMe)-uridine 5',5"-$P^1$,$P^3$,α-boranotriphosphate, 16

The tri-n-butylammonium-tri-n-octylammonium 5-OMe-uridine mono phosphate salt (0.201 mmol) was dissolved in dry DMF (0.4 ml), and added to a flamed-dried, nitrogen-flushed two-necked round bottom flask containing CDI (162.8 mg, 1.005 mmol, 5 eq). The reaction was stirred at RT. After 2 h TLC ($NH_4OH$:$H_2O$:2-propanol 2:7:11) showed the presence of a less polar product ($R_f$=0.62) and the complete disappearance of the starting material ($R_f$=0.35). MeOH (0.07 ml, 1.809 mmol, 9 eq) was added in order to destroy CDI leftovers, and after 10 min, a solution of 13 (0.201 mmol, 1 eq) in dry DMF (1 ml) and $MgCl_2$ (76 mg, 0.804 mmol, 4 eq) were added. The solution was stirred at RT and TLC monitoring after 24 hours showed the presence of a more polar product ($R_f$=0.41) and the complete disappearance of the intermediate. The solution was freeze-dried after the addition of water. The semisolid obtained after freeze-drying was chromatographed on an activated Sephadex DEAD-A25 column. The resin was washed with deionized water and loaded with the crude reaction residue dissolved in a minimal volume of water. The separation was monitored by UV detection (ISCO, UA-6) at 280 nm. A buffer gradient of 0-0.2 M $NH_4HCO_3$ (200 ml of each solution) followed by a second buffer gradient of 0.2-0.4 M $NH_4HCO_3$ (250 ml of each solution) were applied. The different fractions were pooled and freeze-dried three times to yield a white solid. Final separation of the diastereomers and purification of the relevant fractions was carried out on an HPLC system, using a semi-preparative reverse-phase column, under the conditions described bellow. The purity of the nucleotides was evaluated on an analytical reverse-phase column system, in two solvent systems as described below. Finally, aqueous solutions of the products were passed through a Dowex 50WX8-200 ion-exchange resin $Na^+$-form column and the products were eluted with deionized water to obtain the corresponding sodium salts after freeze-drying.

Separation of Diastereoisomers 16A and 16B

The separation of analogue 16 diastereoisomers, 16A and 16B, was accomplished using a semipreparative reverse-phase Gemini 5μ column and isocratic elution with 93:7 (A) 100 mM TEAA, pH 7:(B) $CH_3CN$ at a flow rate of 5 mL/min. Fractions containing purified isomers [$R_f$=6.60 min (16A); 10.87 min (16B isomer)] were collected and freeze-dried. Excess buffer was removed by repeated freeze-drying cycles, with the solid residue dissolved each time in deionized water. Diastereoisomers 16A and 16B were obtained at 45.2% overall yield (74.4 mg) after LC separation.

Characterization of 16A $^1$H NMR ($D_2O$; 600 MHz): δ 7.33 (s, 1H, H-$6_A$), 7.32 (s, 1H, H-$6_B$), 6.02 (d, J=6.3, 1H, H-$1'_A$), 6.02 (d, J=5.6, 1H, H-$1'_B$), 4.37-4.44 (m, 4H, H-$2'_A$, H-$2'_B$, H-$3'_A$, H-$3'_B$), 4.22-4.29 (m, 4H, H-$4'_A$, H-$4'_B$, H-$5'_A$, H-$5'_B$), 4.26 (m, 1H, H-$5"_A$), 4.13 (m, 1H, H-$5"_B$), 3.83 (s, 6H, $CH_{3A}$, $CH_{3B}$), 0.49 (m, 3H, $BH_3$) ppm. $^{31}$P NMR (240 MHz, $D_2O$) δ: 84.29 (m, 1P, $P_α$—$BH_3$), −11.03 (d, J=18.3 Hz, 1P, $P_γ$), −22.52 (dd, J=27.8, J=18.3 Hz, 1P, $P_β$) ppm. HR MALDI (negative) calcd for $C_{20}H_{31}B_1N_4O_{21}P_3$ 767.078 found 767.079. Purity data obtained on an analytical column: retention time: 3.76 min (96.84% purity) using solvent system I isocratic elution of 94:6 A:B over 10 min followed by a gradient from 94:6 to 85:15 over 2 min at a flow rate of 1 ml/min. Retention time: 2.43 min (95.14% purity) isocratic elution of 97.5:2.5 A:B over 8 min followed by a gradient from 97.5:2.5 to 85:15 over 2 min at a flow rate of 1 ml/min.

Characterization of 16B $^1$H NMR ($D_2O$; 600 MHz): δ 7.33 (s, 1H, H-$6_A$), 7.31 (s, 1H, H-$6_B$), 6.02 (m, 1H, H-$1'_A$, H-$1'_B$), 4.35-4.41 (m, 4H, H-$2'_A$, H-$2'_B$, H-$3'_A$, H-$3'_B$), 4.24-4.32 (m, 5H, H-$4'_A$, H-$4'_B$, H-$5'_A$, H-$5'_B$, H-$5"_A$), 4.11 (m, 1H, H-$5"_B$), 3.80 (s, 6H, $CH_{3A}$, $CH_{3B}$), 0.43 (m, 3H, $BH_3$) ppm. $^{31}$P NMR (240 MHz, $D_2O$) δ: 84.05 (m, 1P, $P_α$—$BH_3$), −11.09 (d, J=18.3 Hz, 1P, $P_γ$), −22.55 (dd, J=31.4, J=18.3 Hz, 1P, $P_β$) ppm. HR MALDI (negative) calcd for $C_{20}H_{31}B_1N_4O_{21}P_3$ 767.078 found 767.079. Purity data obtained on an analytical column: retention time: 7.01 min (97.31% purity) using solvent system I isocratic elution of 94:6 A:B over 10 min followed by a gradient from 94:6 to 85:15 over 2 min at a flow rate of 1 ml/min. Retention time: 5.08 min (95.92% purity) isocratic elution of 97.5:2.5 A:B over 8 min followed by a gradient from 97.5:2.5 to 85:15 over 2 min at a flow rate of 1 ml/min.

Example 5

Synthesis of di-(5-OMe)-uridine 5"5"-$P^1$,$P^3$,β-boranotriphosphate, 17

The tri-n-butylammonium-tri-n-octylammonium 5-OMe-uridine mono phosphate salt (401.9 mg, 0.45 mmol) was dissolved in dry DMF (2 ml), and added to a flamed-dried, nitrogen-flushed two-necked round bottom flask containing CDI (364.5 mg, 2.25 mmol, 5 eq). The reaction was stirred at RT. After 2 h TLC (isopropanol: 25% $NH_4OH$: $H_2O$ 11:2:7) showed the presence of a less polar producr ($R_f$=0.62) and the complete disappearance of the starting material ($R_f$=0.35). MeOH (0.09 ml, 2.25 mmol, 5 eq) was added in order to destroy CDI leftovers, and after 10 min, a solution of BPi (523.7 mg, 1.125 mmol, 2.5 eq) in dry DMF (0.5 ml) and $MgCl_2$ (342.7 mg, 3.6 mmol, 8 eq) were added. The solution was stirred at RT and TLC monitoring after 24 hours showed the presence of more polar products and the complete disappearance of the intermediate. The solution was freeze-dried after the addition of water. The semisolid obtained after freeze-drying was chromatographed on an activated Sephadex DEAE-A25 column. The resin was washed with deionized water and loaded with the crude reaction residue dissolved in a minimal volume of water. The separation was monitored by UV detection (ISCO, UA-6) at 280 nm. A buffer gradient of 0-0.2 M $NH_4HCO_3$ (200 ml of each solution) followed by a second buffer gradient of 0.2-0.4 M $NH_4HCO_3$ (300 ml of each solution) were applied. The different fractions were pooled and freeze-dried three times to yield a white solid. Final purification of the relevant fractions was carried out on an HPLC system, using a semi-preparative reverse-phase column, under the conditions described bellow. The purity of the nucleotides was evaluated on an analytical reverse-phase column system, in two solvent systems as described below. Finally, aqueous solutions of the products were passed through a Dowex 50WX8-200 ion-exchange $Na^+$-form resin column and the products were eluted with deionized water to obtain the corresponding sodium salts after freeze-drying.

Purification of 17

The purification of analogue 17 was accomplished using a semipreparative reverse-phase Gemini 5μ column and isocratic elution with 96:4 (A) 100 mM TEAA, pH 7:(B) $CH_3CN$ at a flow rate of 5 ml/min. The fractions containing the purified analogues ($R_t$=6.13 min) were collected and freeze-dried. Excess buffer was removed by repeated freeze-drying cycles, with the solid residue dissolved each time in deionized water. Analogue 17 was obtained at 8% overall yield (30.8 mg) after LC separation.

Characterization of 17

$^1$H NMR ($D_2O$; 600 MHz): δ 7.32 (s, 1H, H-6), 6.02 (m, 2H, H-1'), 4.41 (m, 4H, H-2', H-3'), 4.22 (m, 6H, H-5"), 3.80 (s, 6H, $CH_3$), 0.50 (m, 3H, $BH_3$) ppm. $^{31}$P NMR (240 MHz, $D_2O$) δ: 80.43 (m, 1P, $P_\alpha$—$BH_3$), −7.16 (d, J=29.48 Hz, 1P, $P_\beta$) ppm. HR MALDI (negative) calcd for $C_{20}H_{31}B_1N_4O_{21}P_3$ 767.078 found 767.079. Purity obtained on an analytical column: retention time: 6.09 min (96.33% purity) using solvent system I isocratic elution of 96:4 A:B over 10 min followed by a gradient from 96:4 to 85:15 over 2 min at a flow rate of 1 ml/min. Retention time: 5.34 min (96.12% purity) isocratic elution of 99.5:0.5 A:B over 8 min followed by a gradient from 99.5:0.5 to 85:15 over 2 min at a flow rate of 1 ml/min.

Example 6

Chemical Stability of UDP, 11, 12 and 13A

The stability of UDP, 11, 12 and 13A in a buffer solution (pH 1.4) was evaluated by $^{31}$P NMR at 37° C. for monitoring possible dephosphorylation products (the signal of the phosphate hydrolysis products is at ~0 ppm, while that of the borano phosphate analogues is at ~85 ppm). NMR spectra were recorded on a Bruker DMX-600 spectrometer with a $^{31}$P NMR probe (isotope frequency of 240 MHz) using 85% $H_3PO_4$ as an external reference.

Sodium salts of UDP, 11, 12 and 13A were dissolved in 0.45 ml of KCl/HCl buffer (pH 1.4) and $D_2O$ (0.05 ml) was added. The final pH was adjusted to pH 1.4. pH measurements were performed with an Metrohm pH electrode and a Metrohm 827 meter. Spectra were recorded at 15 min, 1 h, or 24 h time intervals at 37° C. For experiments that were several days long, the solution was kept in an oil bath at 37° C. and spectra were recorded at ca. 24 h time intervals. The phosphate ester hydrolysis rate was determined by measuring the change of the integration of one of the phosphates signals of the starting material with time.

The phosphate ester hydrolysis rate of 13A was determined by measuring the changes in the integration of one of the phosphate signals with time, and fitted a pseudo-first-order reaction model, as shown in FIG. 1. In particular, during the hydrolysis of 13A, we first observed a signal of inorganic phosphate emerging at 0.62 ppm, together with a signal for the remaining boranophosphate of 5-OMe-UMP(α-B) at 96.57 ppm. At the same time, the signals for $P_\beta$ (−10.69 ppm) and $P_\alpha$ (86.55 ppm) of the 13A decreased, indicating that the terminal phosphate was rapidly lost under these conditions. Next, two additional signals appeared at 7.31 and 4.42 ppm indicating the formation of the 5-OMe-uridine-H-phosphonate and inorganic H-phosphonate moieties, respectively. Rate constant of $1.31\times10^{-5}$ s$^{-1}$ ($t_{1/2}$=16.9 h) was established for 13 as compared with $6.66\times10^{-7}$ s$^{-1}$ ($t_{1/2}$=~12 days), $1.14\times10^{-5}$ s$^{-1}$ ($t_{1/2}$=16.8 h) and $6.25\times10^{-7}$ s$^{-1}$ ($t_{1/2}$=~13 days) for UDP, 11 and 12, respectively.

Example 7

Resistance of UDP, 12 and 13A to Degradation by NPP1 and NPP3

In this study, the hydrolysis rate of analogue 13A as compared to UDP and analogue 12, by human NPP1 and NPP3 after incubation at 37° C. in appropriate buffer, was determined.

56.15 μg or 57.78 μg of human NPP1 or NPP3 extract, respectively, was added to 0.575 ml the incubation mixture (1 mM $CaCl_3$, 200 mM NaCl, 10 mM KCl and 100 mM Tris, pH 8.5) and preincubated at 37° C. for 3 min. Reaction was initiated by the addition of 0.015 ml of 4 mM of UDP, 12 or 13A. The reaction was stopped after incubation of 2 h or 3 h with NPP1 or NPP3, respectively, by transferring a 0.1 ml aliquot from the reaction mixture to 0.350 ml ice-cold 1 M perchloric acid. These samples were centrifuged for 1 min at 10000×g. Supernatants were neutralized with 1 M KOH in 4° C. and centrifuged 1 min at 10000×g. The reaction mixture was filtered and freeze-dried. The hydrolysis rates of the analogues UDP, 12 and 13A by NPP1 or NPP3 were determined by measuring the change in the integration of the HPLC peaks for each analogue over time vs. control. The percentage of compound degradation was calculated vs. control, to take into consideration the degradation of the compounds due to the addition of acid to stop the enzymatic reaction. Therefore, each of the samples was compared to a control which was transferred to acid, but to which no enzyme was added. The percentage of degradation was calculated from the area under the curve of the nucleoside monophosphate peak, after subtraction of the control, which is the amount of the nucleoside monophosphate peak formed due to chemical acidic hydrolysis.

TABLE 1 hydrolysis percentage of UDP, 12 and 13A by NPP1 and NPP3

| Analogue | Hydrolysis percentage* | |
|---|---|---|
|  | NPP1 | NPP3 |
| UDP | 50% | 45% |
| 12 | 49% | 36% |
| 13A | 15% | 28% |

*After incubation at 37° C. in buffer (1 mM CaCl$_2$, 200 mM NaCl, 10 mM KCl and 100 mM Tris, pH 8.5) for 2 or 3 h, with NPP1 or NPP3, respectively.
Values represent mean ± S.D. of two experiments (p < 0.05).

As summarized in Table 1, in the presence of NPP1, UDP was 50% hydrolyzed to UMP after 2 h of incubation with the enzyme. Analogue 12 was similarly hydrolyzed to 5-OMe-UMP (49%). Yet, analogue 13A was only 15% hydrolyzed after the same incubation time. Analogue 13A exhibited relative stability also with regard to hydrolysis by NPP3 as compared to analogues UDP and 12, undergoing 28%, 45% and 36% hydrolysis, respectively, to the corresponding nucleoside 5'-monophosphates after incubation of 3 h.

Example 8

Stability of UDP, 11, 12 and 13A in Human Blood Serum

Blood serum contains dephosphorylating enzymes and therefore provides a good model system for estimation of the in vivo stability of nucleotide analogues. In this study, the half-life of analogue 13A in human blood serum as compared to that of UDP, 11 and 12, was determined.

The assay mixture containing 0.1 mg each analogue in deionized water (4.5 μl), human blood serum (180 μl) and RPMI-1640 medium (540 μl) (Eliahu et al., 2010a) was incubated at 37° C. for 0-24 h. At 0.5-12 h intervals, each sample was heated to 80° C. for 30 min, treated with CM Sephadex (1-2 mg), shaken for 2 h and centrifuged for 6 min (12000 rpm), and the aqueous layer was collected and extracted with chloroform (2×500 μl). The aqueous layer was freeze-dried and then dissolved in deionized water (100 μl). Samples were loaded onto an activated Starta X-AW weak anion exchange cartridge, washed with H$_2$O (1 ml) and eluted with MeOH:H$_2$O (1:1, 1 ml) followed by NH$_4$OH:MeOH:H$_2$O (2:25:73, 1 ml), and then freeze-dried. The resulting residue was analyzed by HPLC on a Gemini analytical column (5μ C-18 557 110 A; 150 mm×4.60 mm), using gradient elution with solvent system I (for UDP and 12—A:B 96:4 over 10 min) or II (for uridine-5'-O-(α-borano diphosphate) and 13A—A:B 97.5:2.5 over 10 min) at a flow rate of 1 ml/min. The hydrolysis rates of the analogues UDP, uridine-5'-O-(α-borano diphosphate), 12 and 13A with blood serum were determined by measuring the change in the integration of the HPLC peaks for each analogue over time vs. control. The percentage of compound degradation was calculated vs. control, to take into consideration the degradation of the compounds due to the work up following the enzymatic reaction. Therefore, each of the samples was compared to a control which was put through the same workup, but to which no serum was added. The percentage of degradation was calculated from the area under the curve of the nucleoside monophosphate peak, after subtraction of the control, which is the amount of the nucleoside monophosphate peak formed due to chemical hydrolysis.

Figure 2A:
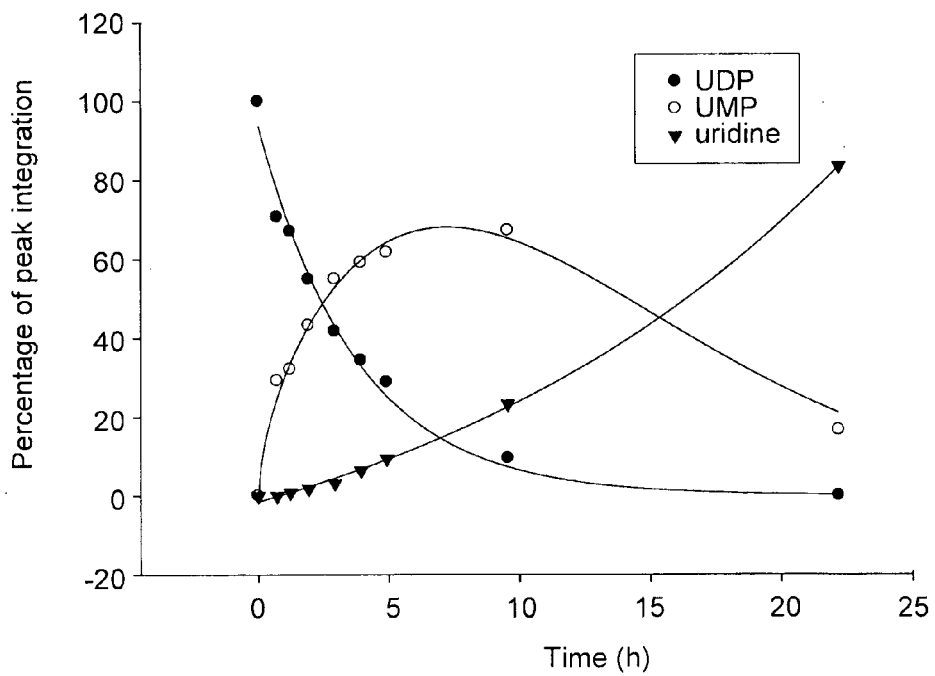
FIGS. 2A-2B show time-dependent hydrolysis curves of UDP (2A) and of 11, 12 and 13A (2B) in human blood serum (180 μl) and RPMI-1640 medium (540 μl) over 24 h at 37° C., as monitored by HPLC.
Figure 2B:
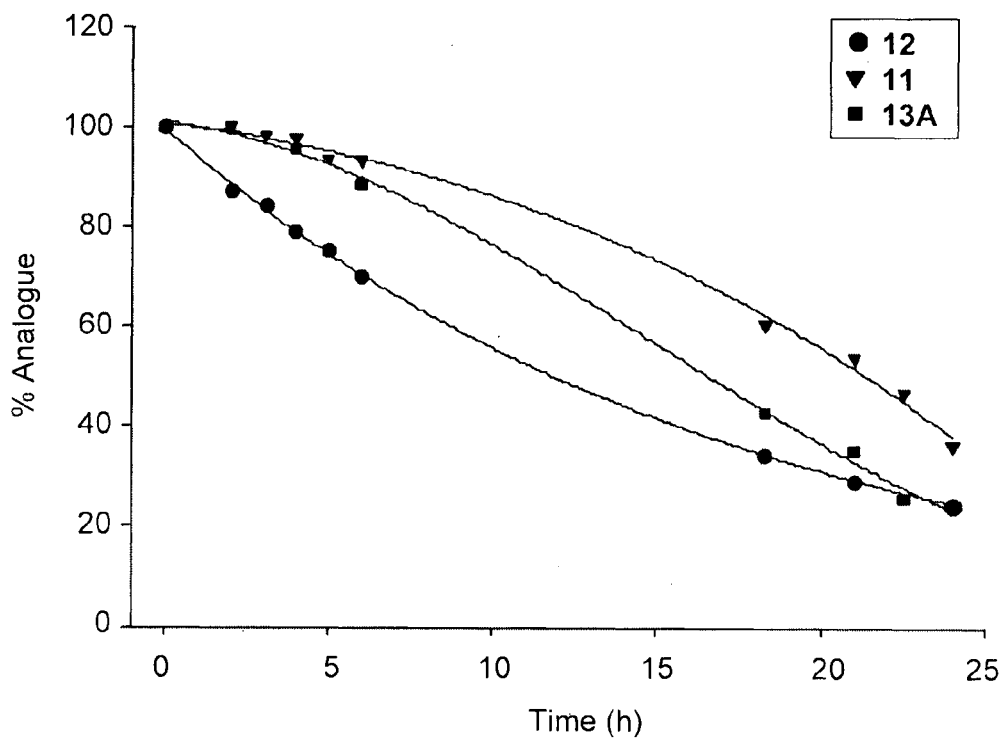

As shown in FIGS. 2A-2B, UDP was hydrolyzed to UMP, followed by further degradation to uridine, with a half-life of 2.4 h (2A). Yet, analogue 12 was hydrolyzed to the corresponding nucleoside 5'-monophosphate and nucleoside with a half-life of 11.9 h, and 11 displayed a half-life of 21 h. 13A was hydrolyzed to 5-OMe-UMP(α-B) and then to 5-OMe-uridine with a half-life of 17 h (2B).

Example 9

Activity of Analogues 13-17 at P2Y$_{2/4/6}$-Receptors

As described in Ginsburg-Shmuel et al. (2010), both 5-methoxyuridine triphosphate (5-OMe-UTP) and 5-methoxyuridine diphosphate (5-OMe-UDP), 12, were found to be agonists of the P2Y$_6$-receptors with EC$_{50}$ of 0.9 and 0.08 μM, respectively.

In this study, analogues 13-17 were tested for their potency and selectivity at P2Y$_{2,4,6}$-receptors based on measurements of increases in intracellular calcium concentrations in 1321N1 astrocytoma cells transfected with the respective plasmid, as described in Materials and Methods, and the results are summarized in Table 2.

TABLE 2

Potencies (EC$_{50}$ in μM) of analogues 13-17 at the P2Y$_{2/4/6}$-receptors in 1321N1 astrocytoma cells

| Receptor subtype | 13 A | 13 B | 14 A | 14 B | 15 | 16 A | 16 B | 17 | UDP | UTP |
|---|---|---|---|---|---|---|---|---|---|---|
| P2Y$_2$-R | n.d.r | n.d.r | n.d.r | n.d.r | n.d.r | n.d.r | n.d.r | n.d.r | — | 0.14 |
| P2Y$_4$-R | n.d.r | n.d.r | n.d.r | n.d.r | n.d.r | n.d.r | n.d.r | n.d.r | — | 0.9 |
| P2Y$_6$-R | 0.008 ± 0.003 | 4.3 ± 1.9 | 11.23 ± 0.63 | 20.11 ± 0.70 | >10$^a$ | 0.06 ± 0.02 | 2.2 ± 0.5 | 0.2 ± 0.04 | 0.15 ± 0.03 | — | n.d.r.—no detectable response for nucleotide concentrations of up to 100 μM.
$^a$for nucleotide concentrations of up to 100 μM it was not possible to calculate an EC$_{50}$ value, since the plateau of the rise of [Ca$^{2+}$]$_i$ was not reached.

Figure 3A:
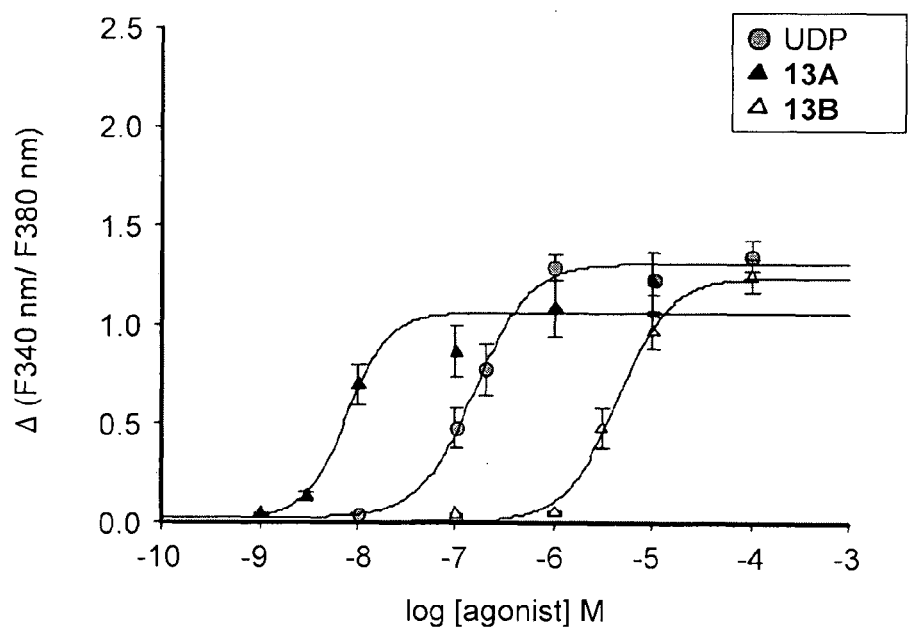
FIGS. 3A-3D show concentration-response curves for nucleotides 13A (3A), 15 (3C), 16 (3B) and 17 (3D), and the endogenous agonist UDP at the P2Y$_6$-R. Data were obtained from 1321N1 cells stably expressing the P2Y$_6$GFP receptor determining the ligand induced change in [Ca$^{2+}$]$_i$. Cells were pre-incubated with 2 μM fura-2 AM for 30 min and change in fluorescence (Δ F340 nm/F380 nm) was detected. Concentration-response curves are from one data set but, for clarity, are represented in separate diagrams with the UDP response curve for common reference.
Figure 3B:
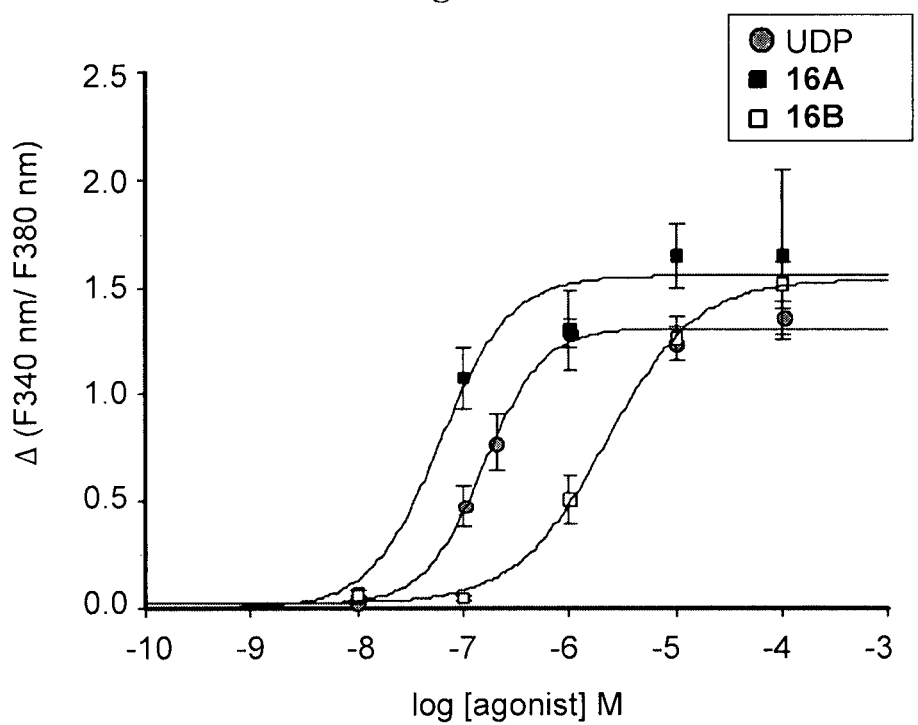

As shown, 13A was a potent and selective agonist at the P2Y$_6$ receptor, when expressed in 1321N1 astrocytoma cells and was more potent than the standard agonist UDP. The introduction of a chiral center in 5-OMe-UDP by BH$_3^-$ substitution of the non-bridging oxygen at Pα reveals stereoselectivity preference of the receptor for the A-isomer over the B-isomer. The A-isomer of the mono-nucleotide derivative 13A (R$_p$ isomer) was the most potent agonist among the tested nucleotides with EC$_{50}$=0.008 μM, and was more than 500-fold more potent than the corresponding B-isomer 13B (EC$_{50}$=4.3 μM, FIG. 3A) and 19-fold more potent than the endogenous agonist UDP (EC$_{50}$=0.15 μM). For the di-nucleotide derivatives of 5-OMe-UDP, 16A and 16B, a similar stereo-selectivity could be observed, although less pronounced, wherein the potency of the A-isomer (R$_p$ isomer) (EC$_{50}$=0.06 μM) was similar to that of UDP (FIG. 3B) but only about 37-fold higher than that of the corresponding B-isomer (EC$_{50}$=2.2 μM).

The preference of P2Y$_6$-R for R$_p$ isomer has not been observed before. However, we have already described diastereoselective properties of P2Y$_1$- and P2Y$_{11}$-receptors which displayed preference for the R$_p$ and S$_p$ isomers of boranophosphate and phosphorothioate adenine nucleotides, respectively (Major et al., 2004; Ecke et al., 2006). Based on our computational studies of P2Y$_1$-R, we previously suggested that a hard Mg$^{2+}$ ion, which is bound to the nucleotide inside the receptor, binds preferentially the hard P$_\alpha$ oxygen atom in ATP-α-B analogues, rather than the borane group. Thus, in the ATP-α-B (S$_p$) isomers, the P$_\alpha$ oxygen is not in a position to coordinate the Mg$^{2+}$ ion, and in this case the coordination occurs probably via P$_{\beta,\gamma}$. Hence, this isomer loses a tight interaction, possibly with Mg$^{2+}$ ion, resulting eventually in its higher EC$_{50}$ values (Major et al., 2004). Similarly, we assume that 13B is less potent than 13A due to loss of binding interactions of P2Y$_6$-R with P$_\alpha$ of 13B.

Although borano-substitution enhanced dramatically the potency of 12 at P2Y$_6$-R, the corresponding triphosphate mono-nucleotide, 14, was hardly active at the P2Y$_6$-R, due to the preference of the receptor for three phosphate negative charges (Jacobson et al., 2009; Shaver et al., 2005). Likewise, at the P2Y$_2$-R, 14 was completely inactive, even though it is similar to the receptor's endogenous agonist, UTP. The inactivity of 14 as opposed to the activity of 5-OMe-UTP at P2Y$_2$-R (EC$_{50}$=2 µM, compared to UTP, EC$_{50}$=0.1 µM) (Ginsburg-Shmuel et al., 2010), implies that P2Y$_2$-R does not tolerate the P$_\alpha$-borano group. This observation was already made before for ATP(α-B) which elicited a very weak response at the P2Y$_2$ receptor, as compared to the endogenous ligands ATP and UTP (Tulapurkar et al., 2004).

Figure 3C:
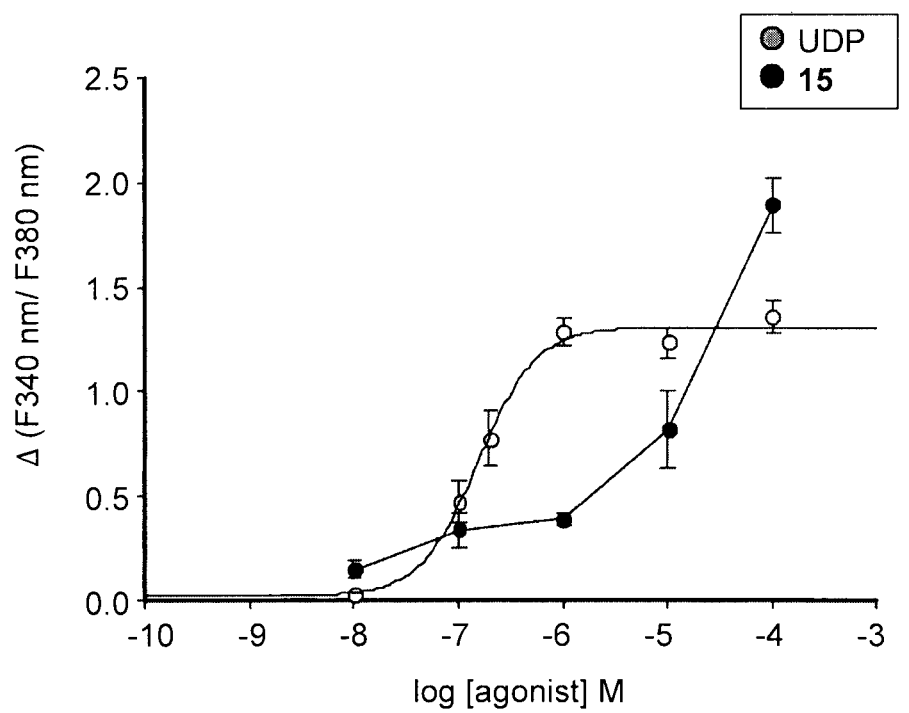
Figure 3D:
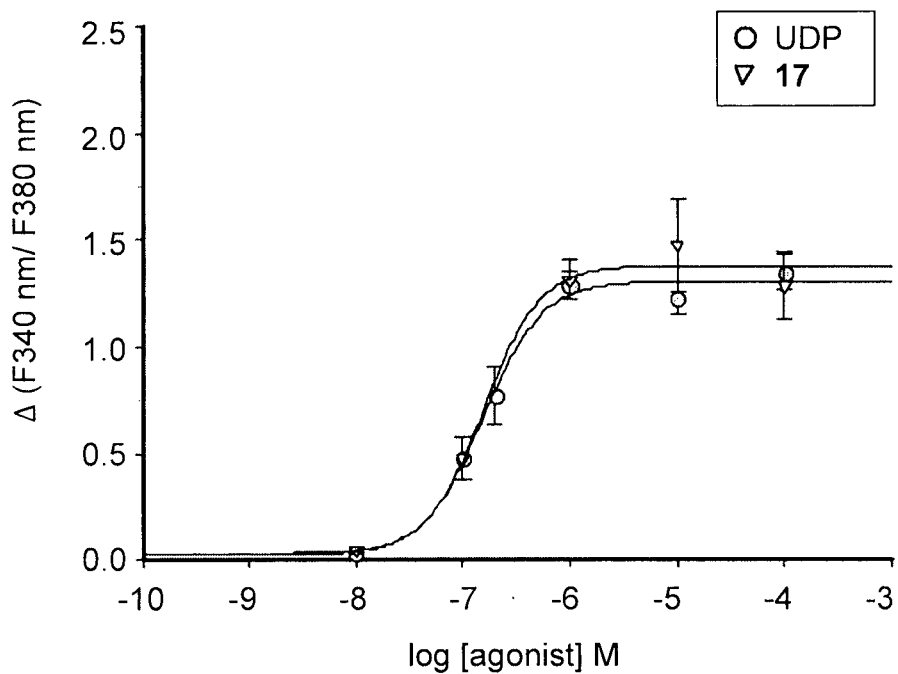

Borano-dinucleotide derivative 16A is about 9-times less potent than its mono-nucleotide counterpart 13A. Analogue 17, a P$_\beta$-borano dinucleotide derivative of 5-OMe-UDP is equipotent to UDP (EC$_{50}$=0.2 µM) (FIG. 3D). Apparently, the decrease in activity of 16A vs. 13A is due to the requirement for a terminal phosphate for molecular recognition by P2Y$_6$-R. Even so, 16A is still more active than 15 or 17 since it is structurally more similar to 13A. The least active P2Y$_6$-R agonist is 15 which is the dinucleotide bearing two methoxy substitutions, one on each of the uracil rings. Surprisingly, this analogue was less active at P2Y$_6$-R than the previously reported dinucleotide triphosphate, Up$_3$U. Apparently, the double 5-OMe substitution in dinucleotide 15 noticeably reduced the potency at the P2Y$_6$ receptor (FIG. 3C). A plateau for the intracellular calcium response could not be reached for nucleotide concentrations of up to 100 µM. Nevertheless, similarly to the mono-nucleotides, the beneficial effect of the borano group in enhancing potency at the P2Y$_6$-R is evident: all borano-bearing nucleotides, either at P$_\alpha$ or P$_\beta$ were far more active than their non-borano counterparts—13A vs. 12, and 16A and 17 vs. 15.

All the tested nucleotides were inactive at the P2Y$_2$-receptor and P2Y$_4$-receptor in 1321N1 cells and at 1321N1 wild type cells, demonstrating specificity.

Example 10

Analogues 12 and 13A Reduce IOP in Normotense Rabbits

Figure 4A:
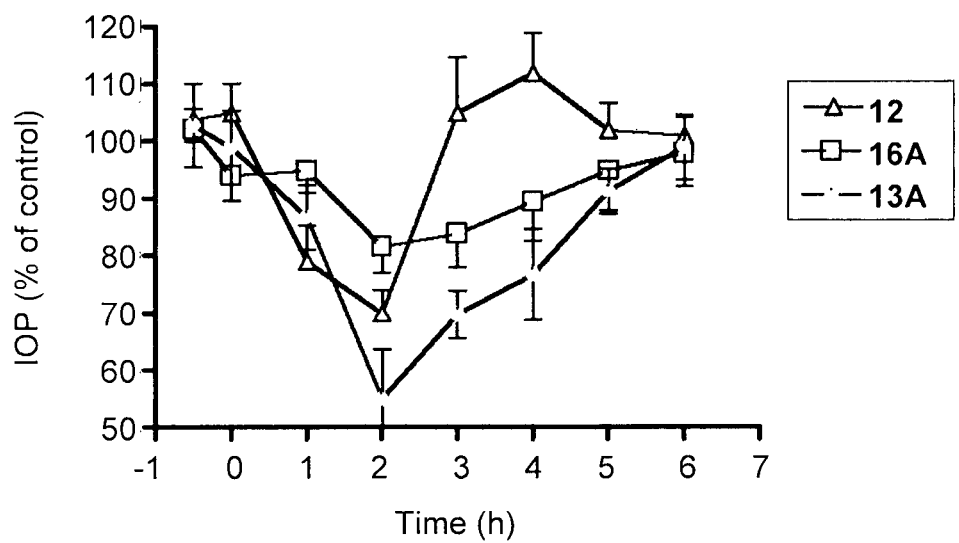
FIGS. 4A-4C show the reduction of intraocular pressure (IOP) in normotense rabbits by the various 5-methoxyuridine nucleotide and dinucleotide derivatives as compared to control, UDP, i.e., the endogenous P2Y$_6$-receptor ligand, and marketed drugs. 4A shows time-course for the effect of compounds 12, 13A and 16A on rabbit IOP measured over 6 h; 4B shows the reduction of KW in normotense rabbits by 12, 13A and 16A vs. UDP and control; and 4C shows the reduction of IOP in normotense rabbits by 12, 13A and 16A vs. Xalatan®, Trusopt®, Pilocarpine and control.
Figure 4B:
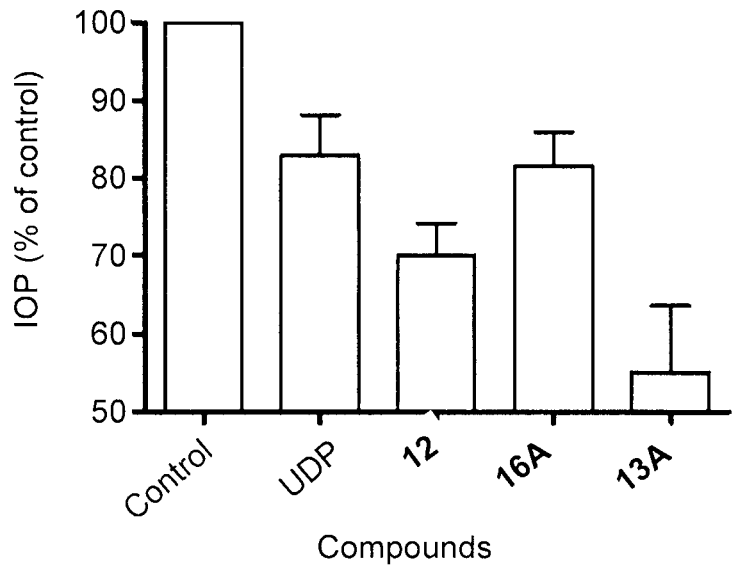
Figure 4C:
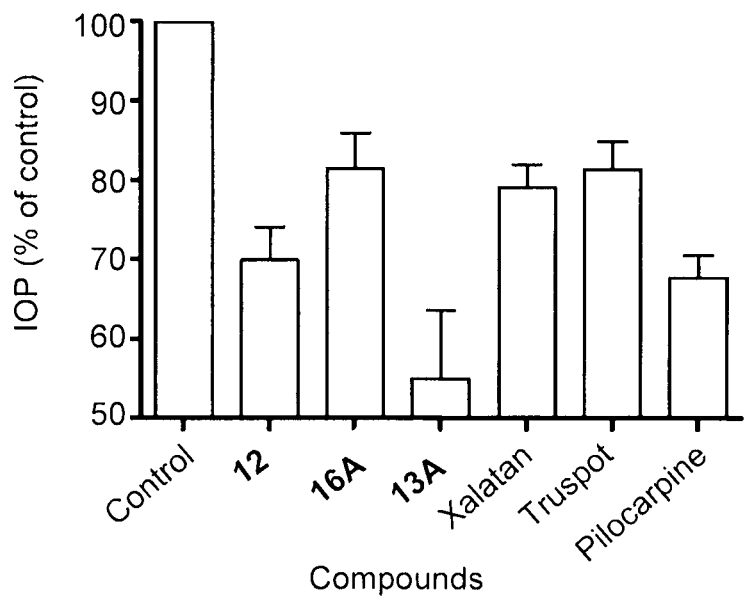

The reduction of intraocular pressure (IOP) in normotense rabbits by the various 5-methoxyuridine nucleotide and dinucleotide derivatives was compared to that of UDP, which is the endogenous P2Y$_6$-receptor ligand, as a control, and to that of certain marketed drugs, and as shown in FIG. 4, analogue 12 reduced IOP by 31%, and analogue 13A reduced IOP by 45%, more than any marketed drug, e.g., Xalatan®, Trusopt®, and Pilocarpine. The duration of action was about 4 h.

APPENDIX

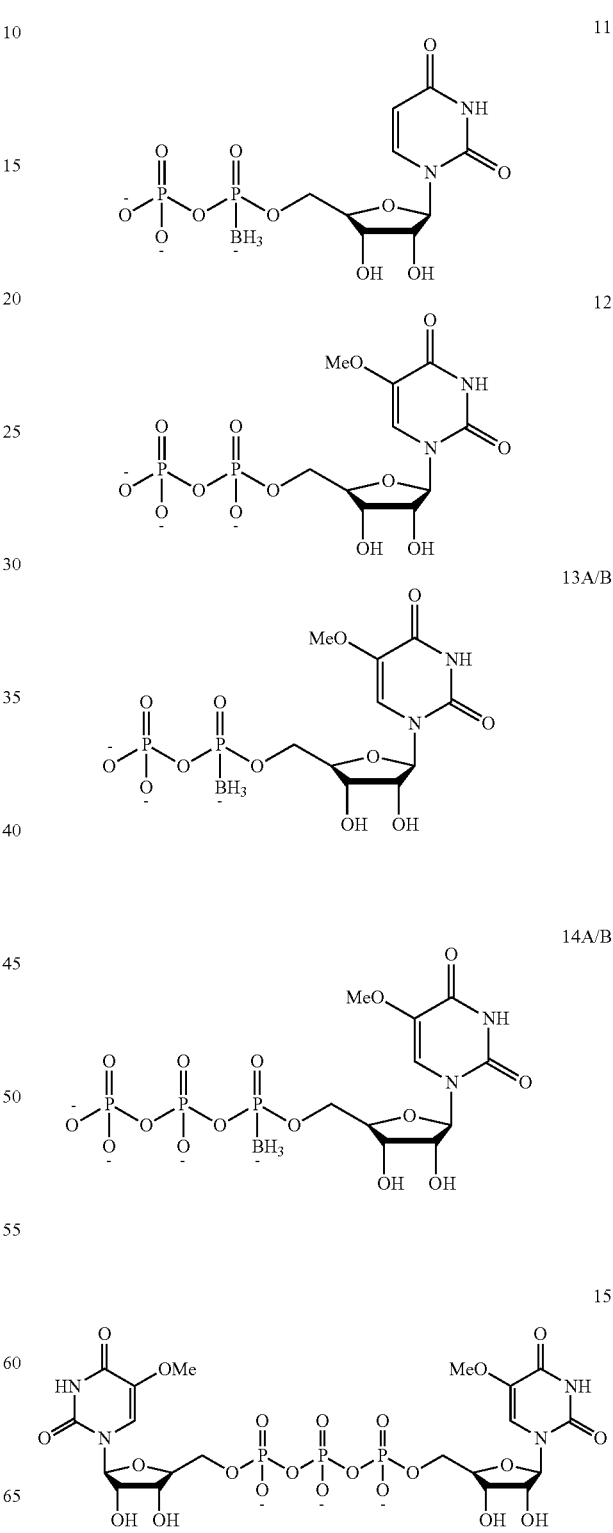

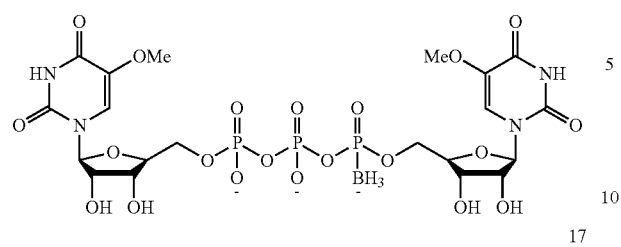
16A/B
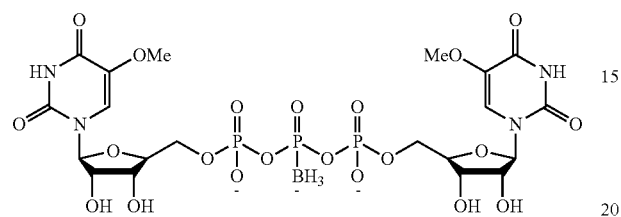
17
Scheme 1: Synthesis of analogues 13 and 14
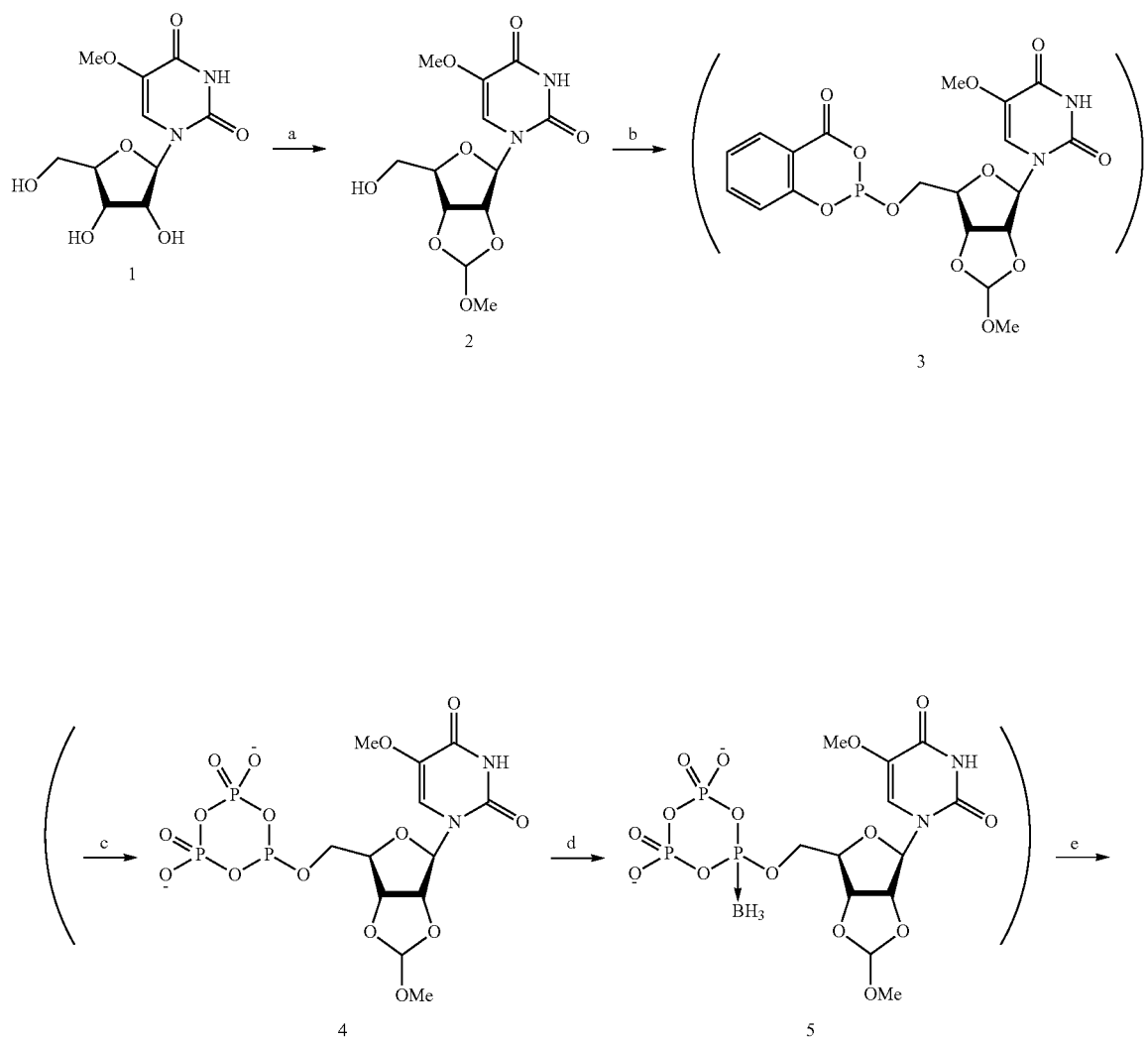

-continued

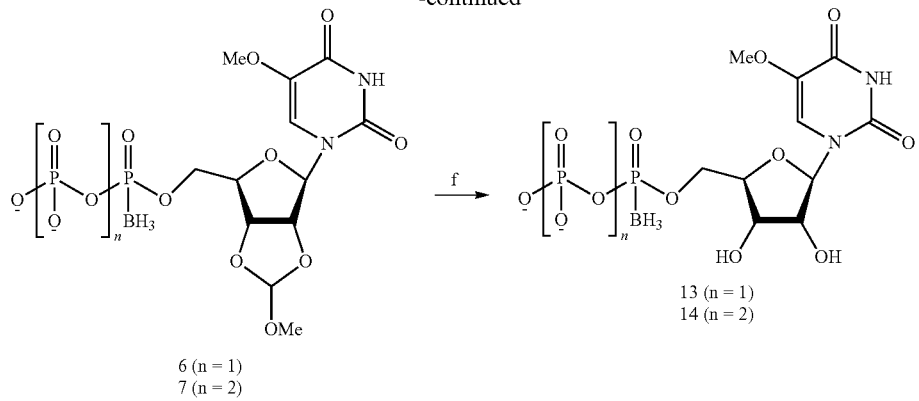

6 (n = 1)
7 (n = 2)

13 (n = 1)
14 (n = 2)

Reaction conditions a) (1) HC(OMe)₃, p-TsOH, RT, overnight; and (2) Dowex (weak base), RT, 3 h, 96.3%; b) 2-Cl-1,3,2-benzdioxaphosphorin-4-one, dry DMF, dry dioxane, RT, 10 min; c) 1M P₂O₇H₂²⁻(Bu₃N⁺H⁺)₂ in dry DMF, Bu₃N, RT, 5 min; and d) 2M BH₃·SMe₂ in THF, RT, 15 min; e) ethylenediamine, RT, 10 min; and f) (1) 10% HCl, pH 2.3, RT, 3 h; and (2) 24% NH₄OH, pH 9, RT, 45 min. Compounds 6 and 7 were obtained as a mixture. Compounds 13 and 14 were obtained in a yield of 50.9% and 9%, respectively, each as a mixture of two diastereoisomers.

REFERENCES

Barral K., Priet S., Sire J., Neyts J., Balzarini J., Canard B., Alvarez K., Synthesis, in vitro antiviral evaluation, and stability studies of novel alpha-borano-nucleotide analogues of 9-[2-(Phosphonomethoxy)ethyl]adenine and (R)-9-[2-(phosphonomethoxy)propyl]adenine. *J. Med. Chem.*, 2006, 49, 7799-7806

Besada P., Shin D. H., Costanzi S., Ko H., Mathe C., Gagneron J., Gosselin G., Maddileti S., Harden T. K., Jacobson K. A., Structure-activity relationships of uridine 5'-diphosphate analogues at the human P2Y₆ receptor. *J. Med. Chem.*, 2006, 49, 5532-5543

Boyle N. A., Rajwanshi V. K., Prhavc M., Wang G., Fagan P., Chen F., Ewing G. J., Brooks J. L., Hurd I., Leeds J. M., Bruice T. W., Cook P. D., Synthesis of 2',3'-dideoxynucleoside 5'-alpha-P-borano-beta,gamma-(di fluoromethylene) triphosphates and their inhibition of HIV-1 reverse transcriptase. *J. Med. Chem.*, 2005, 48, 2695-2700

Burnstock G., Verkhratsky A., Evolutionary origins of the purinergic signalling system. *Acta Physiol.*, 2009, 195, 415-447

Chesterfield J. H., McOmie J. F. W., Tute M. S., Pyrimidines. XI. Synthesis of 5-hydroxypyrimidine and related compounds. *J. Chem. Soc.*, 1960, 4590-4594

Costanzi S., Joshi B. V., Maddileti S., Mamedova L., Gonzalez-Moa M. J., Marquez V. E., Harden T. K., Jacobson K. A., Human P2Y₆ receptor: molecular modeling leads to the rational design of a novel agonist based on a unique conformational preference. *J. Med. Chem.*, 2005, 48, 8108-8111

Crooke A., Guzman-Aranguez A., Peral A., Abdurrahman M. K. A., Pintor J., Nucleotides in ocular secretions: Their role in ocular physiology. *Pharmacol. Ther.*, 2008, 119, 55-73

Crosson C. E., Yates P. W., Bhat A. N., Mukhin Y. V., Husain S., Evidence for multiple P2Y receptors in trabecular meshwork cells. *J. Pharmacol. Exp. Ther.*, 2004, 309, 484-489

Cusack N. J., Hourani S. M. O., Loizou G. D., Welford L. A., Pharmacological effects of isopolar phosphonate analogs of ATP on P2-purinoceptors in guinea pig tenia coli and urinary bladder. *Br. J. Pharmacol.*, 1987, 90, 791-795

Ecke D., Tulapurkar M. E., Nahum V., Fischer B., Reiser G., Opposite diastereoselective activation of P2Y₁ and P2Y₁₁ nucleotide receptors by adenosine 5'-O-(α-boranotriphosphate) analogues. *Br. J. Pharmacol.*, 2006, 149, 416-423

Ecke D., Hanck T., Tulapurkar M. E., Schäefer R., Kassack M., Stricker R., Reiser G., Hetero-oligomerization of the P2Y₁₁ receptor with the P2Y₁ receptor controls the internalization and ligand selectivity of the P2Y₁₁ receptor. *Biochem. J.*, 2008, 409, 107-116

Eliahu S. E., Camden J., Lecka J., Weisman G. A., Sevigny J., Gelinas S., Fischer B., Identification of hydrolytically stable and selective P₂Y₁ receptor agonists. *Eur. J. Med. Chem.*, 2009, 44, 1525-1536

Eliahu S., Martin-Gil A., Perez de Lara M. J., Pintor J., Camden J., Weisman G. A., Lecka J., Sevigny J., Fischer B., 2-MeS-β,γ-CCl2-ATP is a potent agent for reducing intraocular pressure. *J. Med. Chem.*, 2010, 53, 3305-3319

Eliahu S., Barr H. M., Camden J., Weisman G. A., Fischer B, A novel insulin secretagogue based on a dinucleoside polyphosphate scaffold. *J. Med. Chem.*, 2010a, 53, 2472-2481

El-Tayeb A., Qi A., Mueller C. E., Synthesis and structure-activity relationships of uracil nucleotide derivatives and analogues as agonists at human P2Y₂, P2Y₄, and P2Y₆ receptors. *J. Med. Chem.*, 2006, 49, 7076-7087

Gendron F. P., Neary J. T., Theiss P. M., Sun G. Y., Gonzalez F. A., Weisman G. A., Mechanisms of P2X7 receptor-mediated ERK1/2 phosphorylation in human astrocytoma cells. *Am. J. Physiol. Cell Physiol.*, 2003, 284, C571-581

Ginsburg-Shmuel I., Haas M., Schumann M., Reiser G., Kalid O., Stern N., Fischer B., 5-OMe-UDP is a potent and selective P2Y₆-receptor agonist. *J. Med. Chem.*, 2010, 53, 1673-1685

Griffin B. E., Jarman M., Reese C. B., Sulston J. E., The synthesis of oligoribonucleotides. II. Methoxymethylidene derivatives of ribonucleosides and 5'-ribonucleotides. *Tetrahedron*, 1967, 23, 2301-2313

Grobben B., Claes P., Roymans D., Esmans E. L., Van Onckelen H., Slegers H., Ecto-nucleotide pyrophosphatase modulates the purinoceptor-mediated signal transduction and is inhibited by purinoceptor antagonists. *Br. J. Pharmacol.*, 2000, 130, 139-145

Grynkiewicz G., Poenie M., Tsien R. Y., A new generation of Ca²⁺ indicators with greatly improved fluorescence properties. *J. Biol. Chem.*, 1985, 260, 3440-3450

Guzman-Aranguez A., Crooke A., Peral A., Hoyle C. H. V., Pintor J., Dinucleoside polyphosphates in the eye: from physiology to therapeutics. *Prog. Retinal Eye Res.*, 2007, 26, 674-687

Hillmann P., Ko G. Y., Spinrath A., Raulf A., von Kugelgen I., Wolff S. C., Nicholas R. A., Kostenis E., Holtje H. D., Muller C. E., Key determinants of nucleotide-activated G protein-coupled P2Y$_2$ receptor function revealed by chemical and pharmacological experiments, mutagenesis and homology modeling. *J. Med. Chem.*, 2009, 52, 2762-2775

Jacobson K. A., Ivanov A. A., Castro S., Harden T. K., Ko H., Development of selective agonists and antagonists of P2Y receptors. *Purinergic Signal.*, 2009, 5, 75-89

Jacobson K. A., Boeynaems J. M., P2Y nucleotide receptors: promise of therapeutic applications. *Drug Discov. Today*, 2010, 15, 570-578

Joseph S. M., Pifer M. A., Przybylski R. J., Dubyak G. R., Methylene ATP analogs as modulators of extracellular ATP metabolism and accumulation. *Br. J. Pharmacol.*, 2004, 142, 1002-1014

Niedballa U., Vorbruggen H., A general synthesis of N-glycosides. 6. On the mechanism of the stannic chloride catalyzed silyl Hilbert-Johnson reaction. *J. Org. Chem.*, 1976, 41, 2084-2086

Ko H., Carter R. L., Cosyn L., Petrelli R., de Castro S., Besada P., Zhou Y., Cappellacci L., Franchetti P., Grifantini M., Van Calenbergh S., Harden T. K., Jacobson K. A., Synthesis and potency of novel uracil nucleotides and derivatives as P2Y$_2$ and P2Y$_6$ receptor agonists. *Bioorg. Med. Chem.*, 2008, 16, 6319-6332

Kowalska J., Lewdorowicz M., Darzynkiewicz E., Jemielity J., A simple and rapid synthesis of nucleotide analogues containing a phosphorothioate moiety at the terminal position of the phosphate chain. *Tetrahedron Lett.*, 2007, 48, 5475-5479

Major D. T., Nahum V., Wang Y., Reiser G., Fischer B., Molecular Recognition in Purinergic Receptors. 2. Diastereoselectivity of the h-P2Y$_1$-Receptor. *J. Med. Chem.*, 2004, 47, 4405-4416

Maruoka H., Barrett M. O., Ko H., Tosh D. K., Melman A., Burianek L. E., Balasubramanian R., Berk B., Costanzi S., Harden T. K., Jacobson K. A., Pyrimidine ribonucleotides with enhanced selectivity as P2Y$_6$ receptor agonists: novel 4-alkyloxyimino, (S)-methanocarba, and 5'-triphosphate γ-ester modifications. *J. Med. Chem.*, 2010, 53, 4488-4501

Misiura K., Szymanowicz D., Stec W. J., Synthesis of nucleoside α-thiotriphosphates via an oxathiaphospholane approach. *Org. Lett.*, 2005, 7, 2217-2220

Nahum V., Zuendorf G., Levesque S. A., Beaudoin A. R., Reiser G., Fischer B., Adenosine 5'-O-(1-boranotriphosphate) derivatives as novel P2Y$_1$ receptor agonists. *J. Med. Chem.*, 2002, 45, 5384-5396

Nahum V., Fischer B., Boranophosphate salts as an excellent mimic of phosphate salts: preparation, characterization, and properties. *Eur. J. Inorg. Chem.*, 2004, 4124-4131

Niedballa U., Vorbruggen H, A general synthesis of N-glycosides. 6. On the mechanism of the stannic chloride catalyzed silyl Hilbert-Johnson reaction. *J. Org. Chem.*, 1976, 41, 2084-2086

Peral A., Gallar J., Pintor J., Adenine nucleotide effect on intraocular pressure: Involvement of the parasympathetic nervous system. *Exp. Eye Res.*, 2009, 89, 63-70

Pintor J., Peral A., Pelaez T., Martin S., Hoyle C. H. V., Presence of diadenosine polyphosphates in the aqueous humor: Their effect on intraocular pressure. *J. Pharmacol. Exp. Ther.*, 2003, 304, 342-348

Pintor J., Pelaez T., Peral A., Adenosine tetraphosphate, Ap4, a physiological regulator of intraocular pressure in normotensive rabbit eyes. *J. Pharmacol. Exp. Ther.*, 2004, 308, 468-473

Pintor J., Adenine nucleotides and dinucleotides as new substances for the treatment of ocular hypertension and glaucoma. *Curr. Opin. Invest. Drugs*, 2005, 6, 76-80

Shaver S. R., Rideout J. L., Pendergast W., Douglass J. G., Brown E. G., Boyer J. L., Patel R. I., Redick C. C., Jones A. C., Picher M., Yerxa B. R., Structure-activity relationships of dinucleotides: Potent and selective agonists of P2Y receptors. *Purinergic Signal.*, 2005, 1, 183-191

Soto D., Pintor J., Peral A., Gual A., Gasull X., Effects of dinucleoside polyphosphates on trabecular meshwork cells and aqueous humor outflow facility. *J. Pharmacol. Exp. Ther.*, 2005, 314, 1042-1051

Stout M. G., Robins R. K., Synthesis of some 5-methoxypyrimidine nucleosides. *J. Heterocycl. Chem.*, 1972, 9, 545-549

Tulapurkar M. E., Laubinger W., Nahum V., Fischer B., Reiser G., Subtype specific internalization of P2Y$_1$ and P2Y$_2$ receptors induced by novel adenosine 5'-O-(1-boranotriphosphate) derivatives. *Br. J. Pharmacol.*, 2004, 142, 869-878

Tulapurkar M. E. Zundorf G., Reiser G., Internalization and desensitization of a green fluorescent protein-tagged P2Y nucleotide receptor are differently controlled by inhibition of calmodulin-dependent protein kinase II. *J. Neurochem.*, 2006, 96, 624-34

Ubl J. J., Vohringer C., Reiser G., Co-existence of two types of $[Ca^{2+}]_i$-inducing protease-activated receptors (PAR-1 and PAR-2) in rat astrocytes and C6 glioma cells. *Neuroscience*, 1998, 86, 597-609

Yerxa B. R., Sabater J. R., Davis C. W., Stutts M. J., Lang-Furr M., Picher M., Jones A. C., Cowlen M., Dougherty R., Boyer J., Abraham W. M., Boucher R. C., Pharmacology of INS37217 [P1-(uridine 5')-P4-(2'-deoxycytidine 5')tetraphosphate, tetrasodium salt], a next-generation P2Y$_2$ receptor agonist for the treatment of cystic fibrosis. *J. Pharmacol. Exp. Ther.*, 2002, 302, 871-880

Zhou Z., Wang X., Li M., Sohma Y., Zou X., Hwang T. C., High affinity ATP/ADP analogues as new tools for studying CFTR gating. *J. Physiol.*, 2005, 569, 447-457

Zimmermann H., Ectonucleotidases: some recent developments and a note on nomenclature. *Drug Dev. Res.* 2001, 52, 44-56

Zylberg J., Ecke D., Fischer B., Reiser G., Structure and ligand-binding site characteristics of the human P2Y$_{11}$ nucleotide receptor deduced from computational modelling and mutational analysis. *Biochem. J.*, 2007, 405, 277-86

The invention claimed is:

1. A compound of the general formula I:

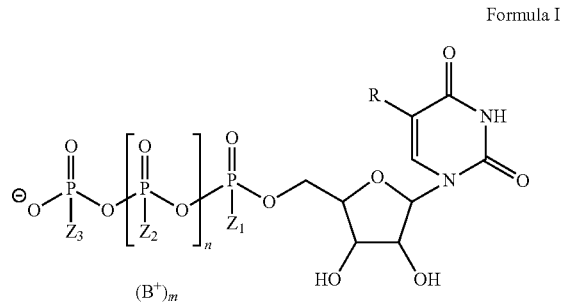

Formula I or a diastereoisomer or mixture of diastereoisomers thereof, wherein

R is —O—($C_1$-$C_8$)alkyl, or —S—($C_1$-$C_8$)alkyl;

$Z_1$, $Z_2$ and $Z_3$ each independently is O$^-$, or $BH_3^-$;

n is 0 or 1;

m is 3 or 4; and

B$^+$ represents a pharmaceutically acceptable cation, but excluding the compounds wherein $Z_1$, $Z_2$, if present, and $Z_3$ are each O$^-$.

2. The compound of claim 1, wherein R is —O—($C_1$-$C_8$)alkyl or —S—($C_1$-$C_8$)alkyl.

3. The compound of claim 1, wherein R is —O—($C_1$-$C_4$)alkyl or —S—($C_1$-$C_4$)alkyl.

4. The compound of claim 1, wherein n is 0, and at least one of $Z_1$ and $Z_3$ is $BH_3^-$; or n is 1, and at least one of $Z_1$ to $Z_3$ is $BH_3^-$.

5. The compound of claim 4, wherein n is 0, and (i) $Z_1$ is $BH_3^-$, and $Z_3$ is O$^-$; (ii) $Z_3$ is $BH_3^-$, and $Z_1$ is O$^-$; or (iii) $Z_1$ and $Z_3$ are $BH_3^-$.

6. The compound of claim 4, wherein n is 1, and (i) $Z_1$ is $BH_3^-$, and $Z_2$ and $Z_3$ are O$^-$; (ii) $Z_2$ is $BH_3^-$, and $Z_1$ and $Z_3$ are O$^-$; (iii) $Z_3$ is $BH_3^-$, and $Z_1$ and $Z_2$ are O$^-$; (iv) $Z_1$ and $Z_2$ are $BH_3^-$, and $Z_3$ is O$^-$; (v) $Z_1$ and $Z_3$ are $BH_3^-$, and $Z_2$ is O$^-$; (vi) $Z_2$ and $Z_3$ are $BH_3^-$, and $Z_1$ is O$^-$; or (vii) $Z_1$ to $Z_3$ are $BH_3^-$.

7. The compound of claim 1, wherein R is —O—($C_1$-$C_4$)alkyl, n is 0, and (i) $Z_1$ is $BH_3^-$, and $Z_3$ is O$^-$; $Z_1$ is O$^-$, and $Z_3$ is $BH_3^-$; or (iii) $Z_1$ and $Z_3$ are $BH_3^-$.

8. The compound of claim 7, wherein R is —OCH$_3$, n is 0, $Z_1$ is $BH_3^-$, and $Z_3$ is O$^-$, herein identified as 5-methoxyuridine-5'-O-(α-boranodiphosphate).

9. The compound of claim 8, which is the isomer of 5-methoxyuridine-5'-O-(α-boranodiphosphate) with a retention time ($R_t$) of 8.97 min when separated from a mixture of diastereoisomers by application of a semi-preparative reverse-phase Gemini 5μ column (C-18 110A, 250×10 mm, 5 micron), and isocratic elution (100 mM triethylammonium acetate, pH 7: CH$_3$CN, 94:6) with flow rate of 5 ml/min.

10. The compound of claim 7, wherein R is —OCH$_3$, n is 1, $Z_1$ is $BH_3^-$, and $Z_2$ and $Z_3$ is O$^-$, herein identified as 5-methoxyuridine-5'-O-(α-boranotriphosphate).

11. The compound of claim 7, wherein R is —OCH$_3$ or —OC$_2$H$_5$.

12. The compound of claim 1, wherein R is —O—($C_1$-$C_4$)alkyl, n is 1, and (i) $Z_1$ is $BH_3^-$, and $Z_2$ and $Z_3$ is O$^-$; (ii) $Z_2$ is $BH_3^-$, and $Z_1$ and $Z_3$ are O$^-$; (iii) $Z_3$ is $BH_3^-$, and $Z_1$ and $Z_2$ are O$^-$; (iv) $Z_1$ and $Z_2$ are $BH_3^-$, and $Z_3$ is O$^-$; (v) $Z_1$ and $Z_3$ are $BH_3^-$, and $Z_2$ is O$^-$; (vi) $Z_2$ and $Z_3$ are $BH_3^-$, and $Z_1$ is O$^-$; or (vii) $Z_1$ to $Z_3$ are $BH_3^-$.

13. The compound of claim 1, wherein B is a cation of an alkali metal, NH$_4^+$, an organic cation of the formula R$_4$N$^+$ wherein each one of the Rs independently is H or $C_1$-$C_{22}$ alkyl, a cationic lipid or a mixture of cationic lipids.

14. A pharmaceutical composition comprising a compound of the general formula I as claimed in claim 1, or a diastereoisomer or mixture of diastereoisomers thereof, and a pharmaceutically acceptable carrier or diluent.

15. A method for reducing intraocular pressure in an individual in need thereof comprising administering to said individual a therapeutically effective amount of a compound of the general formula I in claim 1, or a diastereomer or mixture of diastereoisomers thereof.

16. The method of claim 15, wherein the compound administered is a compound of the general formula I, wherein (i) R is —OCH$_3$, n is 0, $Z_1$ is $BH_3^-$, and $Z_3$ is O$^-$, herein identified as 5-methoxyuridine-5'-O-(α-boranodiphosphate); (ii) R is OCH$_3$, n is 1, $Z_1$ is $BH_3^-$, and $Z_2$ and $Z_3$ is O$^-$, herein identified as 5-methoxyuridine-5'-O-(α-boranotriphosphate); or (iii) R is —OCH$_3$, n is 0, and $Z_1$ and $Z_3$ are O$^-$, herein identified as 5-methoxyuridine diphosphate (5-OMe-UDP).

17. The method of claim 16, wherein the compound administered is a compound of the general formula I, wherein R is —OCH$_3$, n is 0, $Z_1$ is $BH_3^-$, and $Z_3$ is O$^-$, which is the isomer of 5-methoxyuridine-5'-O-(α-boranodiphosphate) with a retention time ($R_t$) of 8.97 min when separated from a mixture of diastereoisomers by application of a semi-preparative reverse-phase Gemini 5μ column (C-18 110A, 250×10 mm, 5 micron), and isocratic elution (100 mM triethylammonium acetate, pH 7: CH$_3$CN, 94:6) with flow rate of 5 ml/min.

18. The method of claim 15, further comprising treatment of intraocular hypertension and/or glaucoma.

19. The method of claim 18, wherein the glaucoma is primary open angle glaucoma, normal pressure glaucoma, acute angle closure glaucoma, absolute glaucoma chronic glaucoma, congenital glaucoma, juvenile glaucoma, narrow angle glaucoma, chronic open angle glaucoma, or simplex glaucoma.

* * * * *